United States Patent
Peyman

(10) Patent No.: US 6,203,538 B1
(45) Date of Patent: Mar. 20, 2001

(54) INTRASTROMAL CORNEAL MODIFICATION

(76) Inventor: Gholam A. Peyman, 123 Walnut St., New Orleans, LA (US) 70118

(*) Notice: Subject to any disclaimer, the term of this patent is extended or adjusted under 35 U.S.C. 154(b) by 0 days.

(21) Appl. No.: 08/940,202

(22) Filed: Sep. 29, 1997

Related U.S. Application Data

(62) Division of application No. 08/552,624, filed on Nov. 3, 1997, now Pat. No. 5,722,971.

(51) Int. Cl.$^7$ .................................................. A61N 5/06
(52) U.S. Cl. ........................ 606/5; 606/3; 606/15; 606/17
(58) Field of Search ............................. 606/3, 5, 10–18; 128/898

(56) References Cited

U.S. PATENT DOCUMENTS

| | | |
|---|---|---|
| 3,982,541 | 9/1976 | L'Esperance, Jr. . |
| 4,298,004 | 11/1981 | Schachar et al. . |
| 4,452,235 | 6/1984 | Reynolds . |
| 4,648,400 * | 3/1987 | Schneider et al. ................ 606/5 |
| 4,655,774 | 4/1987 | Choyce . |
| 4,665,913 | 5/1987 | L'Esperance, Jr. . |
| 4,669,466 | 6/1987 | L'Esperance, Jr. . |
| 4,676,790 | 6/1987 | Kern . |
| 4,678,422 | 7/1987 | York . |
| 4,729,372 | 3/1988 | L'Esperance, Jr. . |
| 4,744,360 | 5/1988 | Bath . |
| 4,799,931 | 1/1989 | Lindstrom . |
| 4,840,175 | 6/1989 | Peyman . |
| 4,903,695 | 2/1990 | Warner et al. . |

(List continued on next page.)

OTHER PUBLICATIONS

*Corneal Surgery* by L. Girard, The C.V. Mosby Publishing Company, London 1981 pp. 107–141.

"Lamellar Corneal Stromectomy for the Operative Treatment of Myopia" by Tadeusz Krwawicz, Notes, Cases, Instruments, pp. 828–833.

"Keratomileusis and Keratophakia in the Surgical Correction of Aphakia" by Barraquer, Cataract Surgery and Special Techniques, pp. 270–289.

"Refractive Keratoplasty: Acute Morphologic Features," by Baumgartner et al., The CLAO Journal—Apr. 1985, vol. II, No. 2, pp. 163–169.

"Epikeratophakia: Techniques, Complications, and Clinical Results" by Werblin, Opthalmology, pp. 45–58.

*Primary Examiner*—David M. Shay
(74) *Attorney, Agent, or Firm*—Alfred N. Goodman; Jeffrey J. Howell

(57) ABSTRACT

A method for modifying the curvature of a live cornea to correct a patient's vision. First, at least one relatively small opening is made in the cornea for inserting a fiber optic cable or micro-cutting tool therein to create a pocket or cavity with first and second opposed internal surfaces. The laser beam or micro-cutting tool can be directed onto one of the first and second internal surfaces, or both, if needed or desired to incrementally and sequentially ablate or remove three-dimensional portions of the cornea. If a laser beam is used, then a flexible template can be inserted into the opening in the cornea for accurately controlling the pattern to be ablated within the cornea. Preferably, the live cornea is then left alone to collapse and obtain its new refractive power by waiting a set period of time. After waiting the set period of time, the cornea is then examined to determine the new refractive power of the cornea. Now, ocular material can be introduced to the cornea to further modify the curvature of the cornea as needed. The ocular material can be either a fluid or a solid lens or a combination thereof. In either case, the ocular material is transparent or translucent material with either a refractive index substantially the same as the intrastromal tissue of the cornea, or a different refractive index from the intrastromal tissue of the cornea.

11 Claims, 16 Drawing Sheets

U.S. PATENT DOCUMENTS

| | | |
|---|---|---|
| 4,961,744 | 10/1990 | Kilmer et al. . |
| 5,063,942 | 11/1991 | Kilmer et al. . |
| 5,196,026 | 3/1993 | Barrett et al. . |
| 5,215,104 | 6/1993 | Steinert . |
| 5,300,118 | 4/1994 | Silvestrini et al. . |
| 5,318,044 | 6/1994 | Kilmer et al. . |
| 5,318,047 | 6/1994 | Davenport et al. . |
| 5,323,788 | 6/1994 | Silvestrini et al. . |
| 5,336,261 | 8/1994 | Barrett et al. . |
| 5,368,604 | 11/1994 | Kilmer et al. . |
| 5,391,201 | 2/1995 | Barrett et al. . |
| 5,403,335 | 4/1995 | Loomas et al. . |
| 5,405,384 | 4/1995 | Silvestrini . |

* cited by examiner

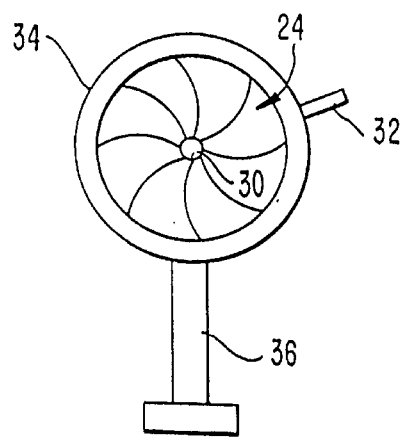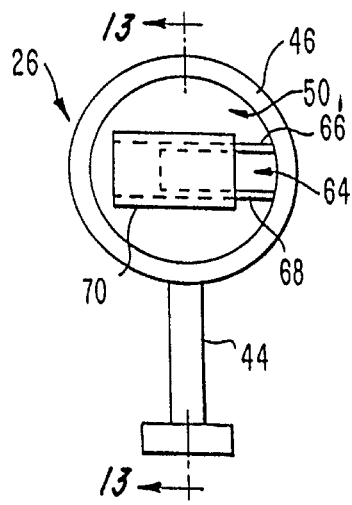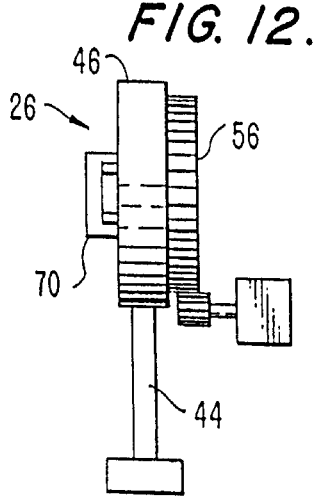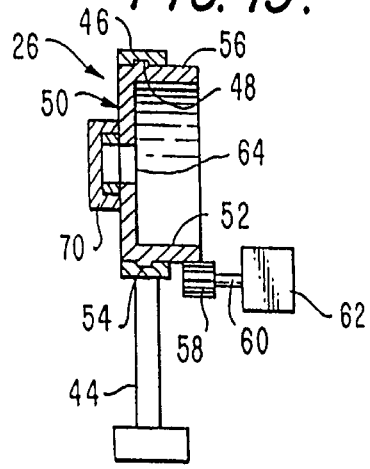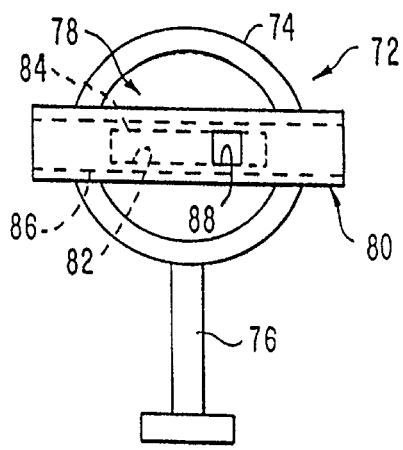

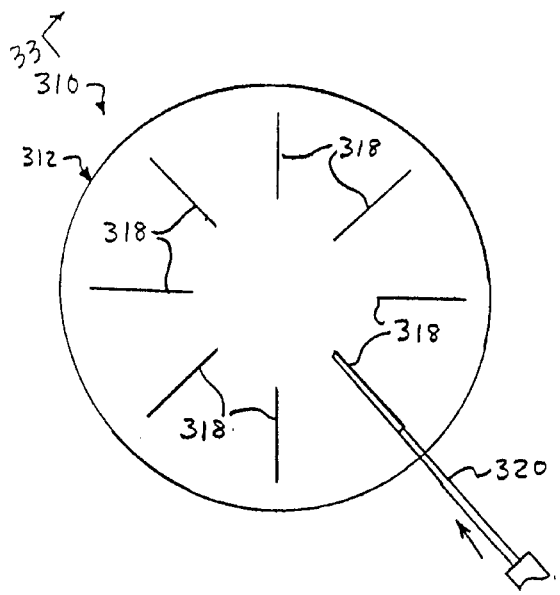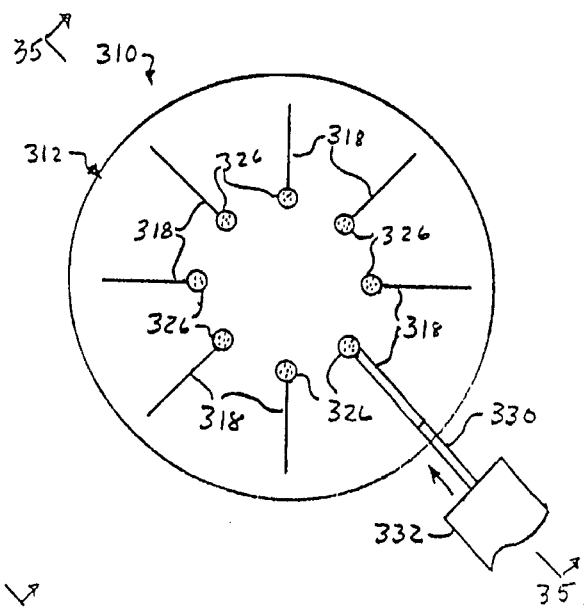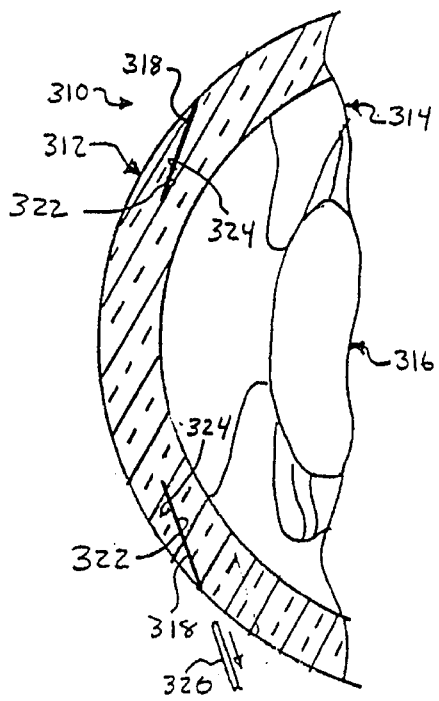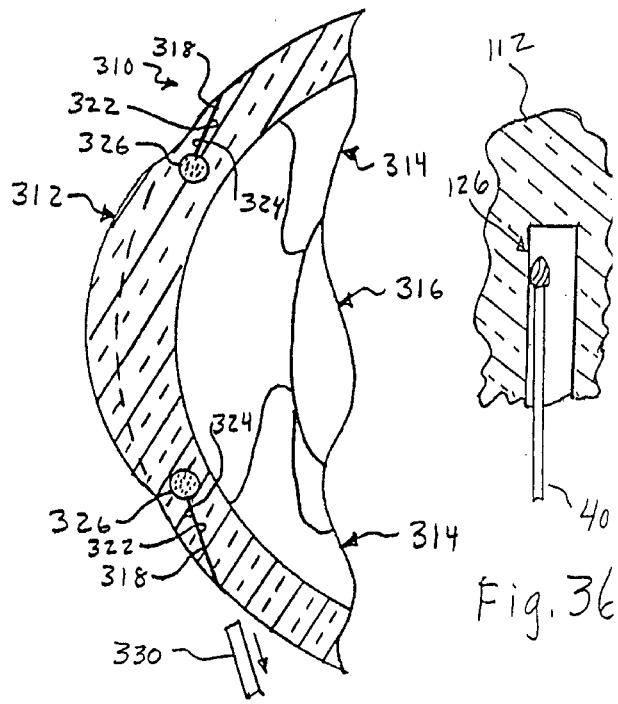
Fig. 32  Fig. 34  Fig. 33  Fig. 35  Fig. 36

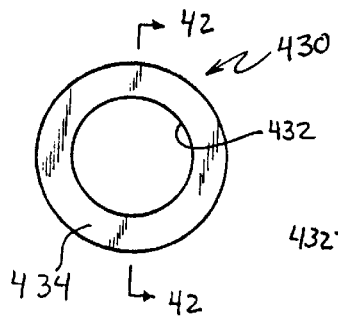
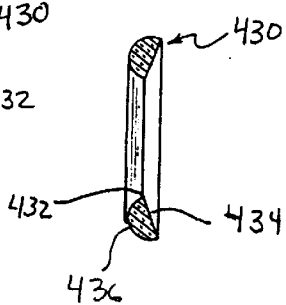
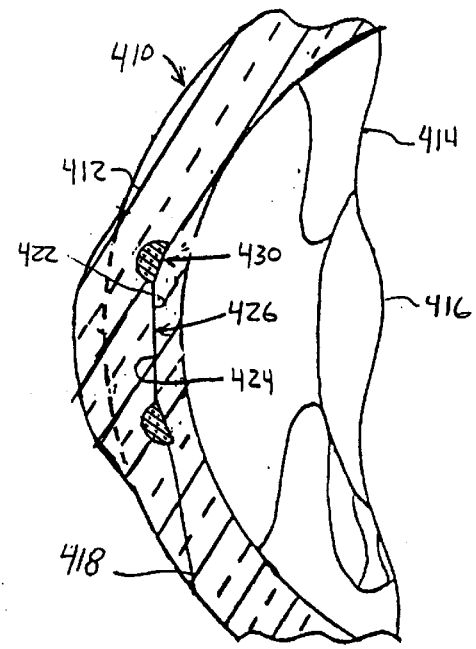
Fig. 41   Fig. 42   Fig. 43
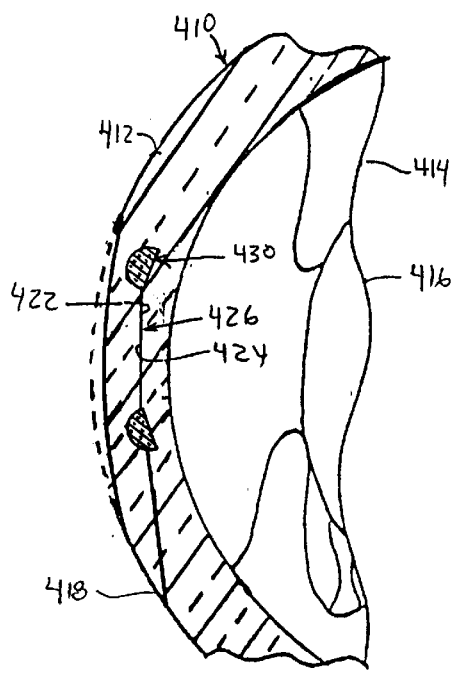
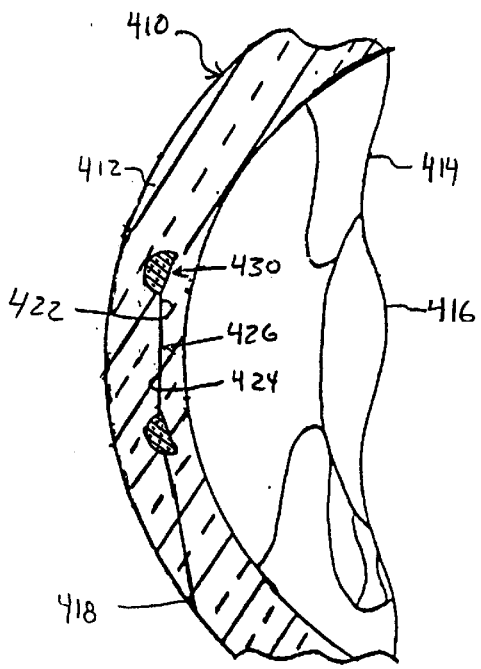
Fig. 44   Fig. 45

INTRASTROMAL CORNEAL MODIFICATION

This is a division of application Ser. No. 08/552,624, filed on Nov. 3, 1997 U.S. Pat. No. 5,722,971.

RELATED APPLICATIONS

This application is a continuation-in-part of applicant's pending application Ser. No. (RABG-32850), filed Oct. 20, 1995, which is related to applicant's pending application Ser. No. 07/844,879, filed Mar. 3, 1992, which is a continuation of application Ser. No. 07/425,928, filed Oct. 24, 1989, now abandoned, which is a continuation-in-part of application Ser. No. 07/370,095, filed Jun. 22, 1989, now abandoned, which is a continuation of application Ser. No. 07/221,011, filed Jul. 18, 1988, now abandoned, which is a continuation of application Ser. No. 06/866,302, filed May 23, 1986, now abandoned, which is a division of application Ser. No. 06/760,080, filed Jul. 29, 1985, now abandoned.

FIELD OF THE INVENTION

The invention relates to methods for modifying a live cornea to change a patient's vision. In particular, the live cornea is modified by the steps of separating an internal area of the live cornea into first and second opposed internal surfaces, and then removing intrastromal tissue and/or introducing transparent optical material between the internal surfaces.

BACKGROUND OF THE INVENTION

In an ametropic human eye, the far point, i.e., infinity, is focused on the retina. Ametropia results when the far point is projected either in front of the retina, i.e., myopia, or in the back of this structure, i.e., hypermetropic or hyperopic state.

In a myopic eye, either the axial length of the eye is longer than in a normal eye, or the refractive power of the cornea and the lens is stronger than in ametropic eyes. In contrast, in hypermetropic eyes the axial length may be shorter than normal or the refractive power of the cornea and lens is less than in a normal eye. Myopia begins generally at the age of 5–10 and progresses up to the age of 20–25. High myopia greater than 6 diopter is seen in 1–2% of the general population. The incidence of low myopia of 1–3 diopter can be up to 10% of the population.

The incidence of hypermetropic eye is not known. Generally, all eyes are hypermetropic at birth and then gradually the refractive power of the eye increases to normal levels by the age of 15. However, a hypermetropic condition is produced when the crystalline natural lens is removed because of a cataract.

Correction of myopia is achieved by placing a minus or concave lens in front of the eye, in the form of glasses or contact lenses to decrease the refractive power of the eye. The hypermetropic eye can be corrected with a plus or convex set of glasses or contact lenses. When hypermetropia is produced because of cataract extraction, i.e., removal of the natural crystalline lens, one can place a plastic lens implant in the eye, known as an intraocular lens implantation, to replace the removed natural crystalline lens.

Surgical attempts to correct myopic ametropia dates back to 1953 when Sato tried to flatten the corneal curvature by performing radial cuts in the periphery of a corneal stroma (Sato, Am. J. Ophthalmol. 36:823, 1953). Later, Fyoderov (Ann. Ophthalmol. 11:1185, 1979) modified the procedure to prevent postoperative complications due to such radial keratotomy. This procedure is now accepted for correction of low myopia for up to 4 diopter (See Schachar [eds] Radial Keratotomy LAL, Pub. Denison, Tex., 1980 and Sanders D [ed] Radial Keratotomy, Thorofare, N.J., Slack publication, 1984).

Another method of correcting myopic ametropia is by lathe cutting of a frozen lamellar corneal graft, known as myopic keratomileusis. This technique may be employed when myopia is greater than 6 diopter and not greater than 18 diopter. The technique involves cutting a partial thickness of the cornea, about 0.26–0.32 mm, with a microkeratome (Barraquer, Ophthalmology Rochester 88:701, 1981). This cut portion of the cornea is then placed in a cryolathe and its surface modified. This is achieved by cutting into the corneal parenchyma using a computerized system. Prior to the cutting, the corneal specimen is frozen to −18° F. The difficulty in this procedure exists in regard to the exact centering of the head and tool bit to accomplish the lathing cut. It must be repeatedly checked and the temperature of the head and tool bit must be exactly the same during lathing. For this purpose, carbon dioxide gas plus fluid is used. However, the adiabatic release of gas over the carbon dioxide liquid may liberate solid carbon dioxide particles, causing blockage of the nozzle and inadequate cooling.

The curvature of the corneal lamella and its increment due to freezing must also be calculated using a computer and a calculator. If the corneal lamella is too thin, this results in a small optical zone and a subsequent unsatisfactory correction. If the tissue is thicker than the tool bit, it will not meet at the calculated surface resulting in an overcorrection.

In addition, a meticulous thawing technique has to be adhered to. The complications of thawing will influence postoperative corneal lenses. These include dense or opaque interfaces between the corneal lamella and the host. The stroma of the resected cornea may also become opaque (Binder Arch Ophthalmol 100:101, 1982 and Jacobiec, Ophthalmology [Rochester] 88:1251, 1981; and Krumeich J H, Arch, AOO, 1981). There are also wide variations in postoperative uncorrected visual acuity. Because of these difficulties, not many cases of myopic keratomileusis are performed in the United States.

Surgical correction of hypermetropic keratomycosis involves the lamellar cornea as described for myopic keratomileusis. The surface of the cornea is lathe cut after freezing to achieve higher refractive power. This procedure is also infrequently performed in the United States because of the technical difficulties and has the greatest potential for lathing errors. Many ophthalmologists prefer instead an alternative technique to this procedure, that is keratophakia, i.e., implantation of a lens inside the cornea, if an intraocular lens cannot be implanted in these eyes.

Keratophakia requires implantation of an artificial lens, either organic or synthetic, inside the cornea. The synthetic lenses are not tolerated well in this position because they interfere with the nutrition of the overlying cornea. The organic lenticulas, though better tolerated, require frozen lathe cutting of the corneal lenticule.

Problems with microkeratomies used for cutting lamellar cornea are irregular keratectomy or perforation of the eye. The recovery of vision is also rather prolonged. Thus, significant time is needed for the implanted corneal lenticule to clear up and the best corrective visions are thereby decreased because of the presence of two interfaces.

Application of ultraviolet and shorter wavelength lasers also have been used to modify the cornea. These lasers are commonly known as excimer lasers which are powerful sources of pulsed ultraviolet radiation. The active medium of these lasers are composed of the noble gases such as argon, krypton and xenon, as well as the halogen gases such as fluorine and chlorine. Under electrical discharge, these gases react to build excimer. The stimulated emission of the excimer produces photons in the ultraviolet region.

Previous work with this type of laser has demonstrated that far ultraviolet light of argon-fluoride laser light with the wavelength of 193 nm. can decompose organic molecules by breaking up their bonds. Because of this photoablative effect, the tissue and organic and plastic material can be cut without production of heat, which would coagulate the tissue. The early work in ophthalmology with the use of this type of laser is reported for performing radial cuts in the cornea in vitro (Trokel, Am. J. Ophthalmol 1983 and Cotliar, Ophthalmology 1985). Presently, all attempts to correct corneal curvature via lasers are being made to create radial cuts in the cornea for performance of radial keratotomy and correction of low myopia.

Because of the problems related to the prior art methods, there is a continuing need for improved methods to correct eyesight.

SUMMARY OF THE INVENTION

Accordingly, one object of the present invention to provide a method for modifying corneal curvature via introducing a transparent optical material into an internal portion of the cornea.

Another object of the invention is to provide a method for modifying corneal curvature by using a source of laser light in a precise manner via a template and introducing a transparent optical material into the stroma of the cornea if necessary.

Another object of the invention is to provide such a method that can modify the curvature of a live cornea, thereby eliminating the need and complications of working on a frozen cornea.

Another object of the invention is to provide a method for improving eyesight without the use of glasses or contact lenses, but rather by merely modifying the corneal curvature.

Another object of the invention is to provide a method that can modify the curvature of a live cornea without the need of sutures.

Another object of the invention is to provide a method that can modify the curvature of a live cornea with minimal incisions into the epithelium and Bowman's layer of the cornea.

Another object of the invention is to provide a method for modifying the corneal curvature by ablating or coagulating the corneal stroma and introducing a transparent optical material into the stroma of the cornea.

The foregoing objects are basically attained by a method of modifying the curvature of a patient's live cornea having an exterior surface, comprising the steps of forming a relatively small opening in the exterior surface of the live cornea, separating an internal area of the live cornea into first and second opposed internal surfaces via the opening to form a pocket, the first internal surface facing in a posterior direction of the live cornea and the second internal surface facing in an anterior direction of the live cornea, inserting a template through the opening in the exterior surface of the live cornea, the template having a laser beam transmitting portion and a laser beam blocking portion for forming a predetermined template pattern, inserting a portion of a laser beam-emitting cable through the opening between the first and second internal surfaces, directing a laser beam from the laser beam-emitting cable onto the template so that the laser beam passes through the laser beam transmitting portion of the template and onto at least one of the first and second internal surfaces in a predetermined pattern to incrementally ablate and completely remove three-dimensional portions sequentially thereof, and permitting the pocket, after ablation, to collapse and the live cornea to heal.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring now to the drawings which form a part of this original disclosure:

FIG. 10 is a front elevational view of the adjustable diaphragm shown in FIG. 3 used for directing the laser beam towards the eye;

FIG. 11 is a front elevational view of the guiding mechanism shown in FIG. 3 having a rotatable orifice of variable size formed therein, for directing the laser beam towards the eye in a predetermined pattern;

FIG. 12 is a right side elevational view of the guiding mechanism shown in FIG. 11;

FIG. 13 is a right side elevational view in section taken along line 13—13 in FIG. 11 showing the internal parts of the guiding mechanism;

FIG. 14 is a front elevational view of a modified guiding mechanism including a movable orifice;

FIG. 32 is a front elevational view of a live cornea in which a plurality of radially extending cuts have been made with a spatula to separate the cornea at each of the radially extending cuts into first and second opposed internal surfaces in accordance with the present invention;

FIG. 33 is a side elevational view in section taken along line 33—33 of the cornea of FIG. 32 with the spatula removed;

FIG. 34 is a front elevational view of a cornea that has been radially cut as shown in FIGS. 32 and 33 with coagulation conducted at the ends of the radial cuts by a laser, thereby increasing the curvature of the central portion of the cornea;

FIG. 35 is a side elevational view in section taken along line 35—35 of the cornea of FIG. 34 with the laser removed and coagulation conducted at the ends of the radial cuts to increase the curvature of the central portion of the cornea;

FIG. 36 is an enlarged, partial cross-sectional view of a cornea with a drill tip removing tissue therefrom;

FIG. 41 is a rear elevational view of an ocular implant or material in accordance with the present invention for implanting into a cornea;

FIG. 42 is a cross-sectional view of the ocular implant or material illustrated in FIG. 41 taken along section line 42—42;

FIG. 43 is an enlarged side elevational view in section taken through the center of an eye showing the intrastromal pocket with the ocular implant or material of FIGS. 41 and 42 therein for increasing the curvature of the central portion of the cornea;

FIG. 44 is an enlarged side elevational view in section taken through the center of an eye showing the intrastromal pocket with the ocular implant or material of FIGS. 41 and 42 therein for decreasing the curvature of the central portion of the cornea;

FIG. 45 is an enlarged side elevational view in section taken through the center of an eye showing the intrastromal pocket with the ocular implant or material of FIGS. 41 and 42 therein for maintaining the original curvature of the central portion of the cornea;

DETAILED DESCRIPTION OF THE INVENTION

Figure 1:
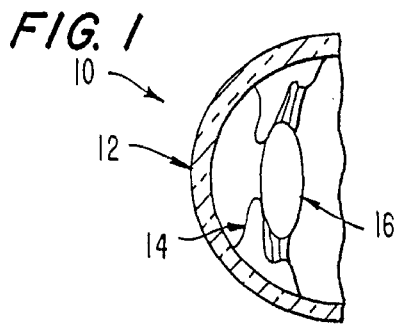
FIG. 1 is a side elevational view in section taken through the center of an eye showing the cornea, pupil and lens.
Figure 2:
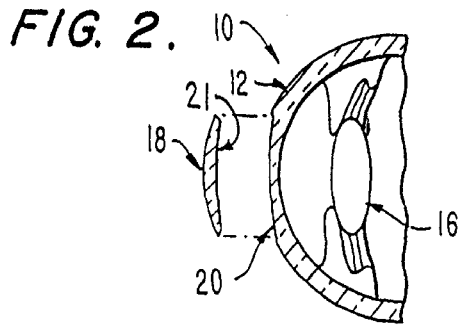
FIG. 2 is a side elevational view in section similar to that shown in FIG. 1 except that a thin layer has been removed from the front of the cornea, thereby separating the cornea into first and second opposed internal surfaces.
Figure 18:
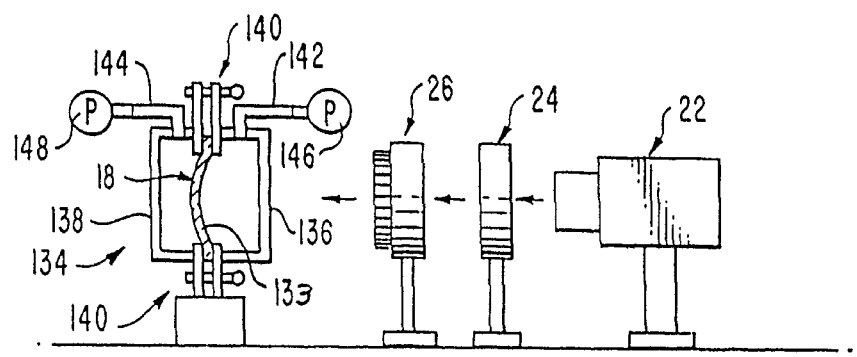
FIG. 18 is a diagrammatic side elevational view of a laser source, diaphragm and guiding mechanism for use in ablating the thin layer removed from the cornea, which is shown supported by a pair of cups.

As seen in FIG. 1, an eye 10 is shown comprising a cornea 12, a pupil 14, and a lens 16. If the combination of the cornea and lens does not provide adequate vision, the cornea can be modified in accordance with the invention to modify the refractive power of the combined corneal and lens system, to thereby correct vision. This is accomplished first by removing a thin layer 18 from the center part of a patient's live cornea 12 by cutting via a means for removing 19, such as a scalpel, via cutting, this thin layer being on the order of about 0.2 mm in thickness with the overall cornea being about 0.5 mm in thickness. Once the thin layer 18 is cut and removed from the cornea, it exposes first and second opposed internal surfaces 20 and 21 resulting from the surgical procedure. Advantageously, it is the exposed internal surface 20 on the remaining part of the cornea that is the target of the ablation via the excimer laser. On the other hand, the cut internal surface 21 on the removed thin layer of the cornea can also be the target of the laser, as illustrated in FIG. 18 and discussed in further detail hereinafter.

Figure 3:
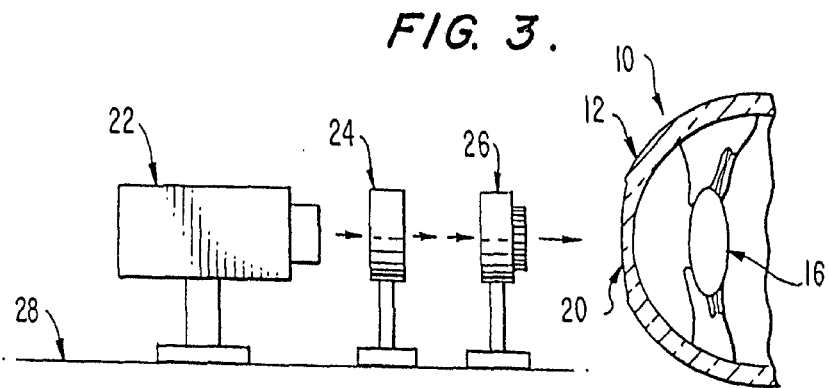
FIG. 3 is a diagrammatic side elevational view of the eye shown in FIG. 2 with a laser beam source, diaphragm and guiding mechanism being located adjacent thereto.

As seen in FIG. 3, the apparatus used in accordance with the invention comprises a source of a laser beam 22, an adjustable diaphragm 24, and a guiding mechanism 26, all aligned adjacent the eye 10 and supported on a suitable base 28.

The laser beam source 22 is advantageously an excimer laser of the argon-fluoride or krypton-fluoride type. This type of laser will photoablate the tissue of the cornea, i.e., decompose it without burning or coagulating which would unduly damage the live tissue. This ablation removes desired portions of the cornea and thereby allows for modification of the curvature thereof.

The adjustable diaphragm 24 seen in FIGS. 3 and 10 is essentially a conventional optical diaphragm with an adjustable central orifice 30 that can be increased or decreased in radial size by a manipulation of a lever 32 coupled to the diaphragm. The diaphragm is advantageously supported in a ring 34 that is in turn supported on a stand 36 on base 28. The material forming the diaphragm is opaque to laser light and thus when the laser is directed towards the diaphragm, it will pass therethrough only via the orifice 30. The diaphragm 24 can be used in conjunction with the guiding mechanism 26, to be described in more detail hereinafter, to restrict the size of the laser beam passing to the guiding mechanism 26, or it can be used by itself to provide ablation of the exposed internal surface 20 of a cornea at its center.

Figure 7:
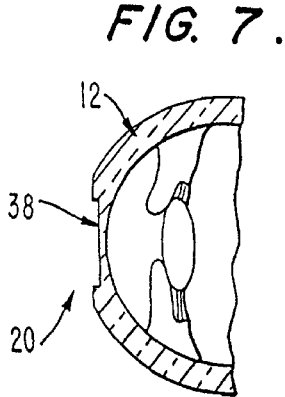
FIG. 7 is a side elevational view in section of an eye which has been ablated in the central area of the internal surface on the cornea.
Figure 8:
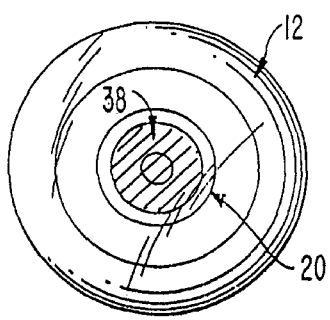
FIG. 8 is a front elevational view of the cornea having the central ablated portion shown in FIG. 7.
Figure 9:
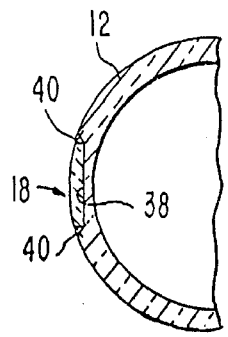
FIG. 9 is a side elevational view in section of the ablated cornea of FIGS. 7 and 8 in which the thin layer previously removed from the cornea is replaced over the ablated area, thereby reducing the curvature of the overall cornea.

This is illustrated in FIGS. 7–9 where a substantially disc-shaped ablated portion 38 is formed in the central exposed internal surface 20 by directing the laser beam 22 through orifice 30 of the diaphragm 24. By modifying the size of the orifice, the disc-shaped ablated portion 38 can be varied in size. Also, by varying the size of the orifice over time, either a concave or convex ablated portion can be formed, as desired. As shown in FIG. 9, once the ablated portion 38 is as desired, the previously removed thin layer 18 is replaced onto the cornea in the ablated portion 38 and can be connected thereto via sutures 40.

Because the ablated portion 38 as seen in FIG. 7 is essentially a uniform cylindrical depression in the exposed internal surface 20, when the thin corneal layer 18 is replaced, the curvature of the cornea is decreased, thereby modifying the refractive power of the cornea and lens system.

As seen in FIG. 10, lever 32 is used to vary the size of orifice 30, and is capable of being manipulated by hand or by a suitable conventional motor, which can be coordinated to provide an expansion or contraction of the orifice as necessary over time.

As seen in FIGS. 3, 11, 12 and 13, the guiding mechanism 26 can be utilized in addition to or in place of the diaphragm 24 to guide the laser light onto the cornea. This guiding mechanism 26 is especially advantageous for forming an annular ablated portion 42 in surface 20 as seen in FIGS. 4–6 for increasing the overall curvature of the cornea.

Figure 4:
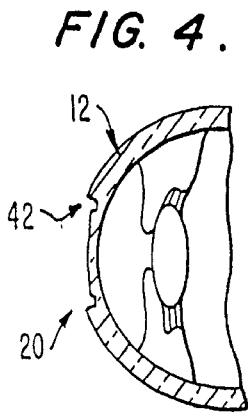
FIG. 4 is a side elevational view in section of an eye that has been treated by the apparatus shown in FIG. 3 with ablation conducted in an annular area spaced from the center of the internal surface on the cornea.
Figure 5:
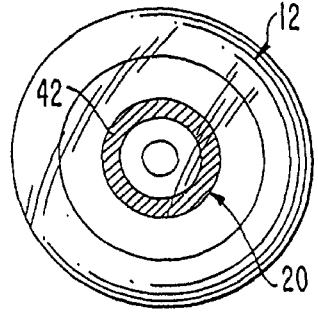
FIG. 5 is a front elevational view of the ablated cornea shown in FIG. 4.
Figure 6:
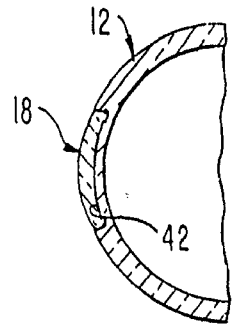
FIG. 6 is a side elevational view in section showing the ablated cornea of FIGS. 4 and 5 with the thin layer previously removed from the cornea replaced onto the ablated area in the cornea, thereby increasing the curvature of the overall cornea.

As seen in FIGS. 4 and 5, this annular ablated portion 42 is spaced from the center of the exposed internal surface 20 and when the previously removed thin corneal layer 18 is replaced and sutured, the thin layer tends to be more convex, thereby modifying the overall curvature of the cornea.

As seen in FIGS. 11–13, the guiding mechanism 26 comprises a stand 44 supporting a ring 46, this ring having a radially inwardly facing recess 48 therein. A disc 50, which is opaque to laser light, is located inside the ring and has a cylindrical extension 52 with an outwardly facing flange 54 rotatably and slidably received in the recess. On the cylindrical extension 52 which extends past ring 46 is an exterior toothed gear 56 that is in engagement with a pinion 58 supported on a shaft 60 of a motor 62. Rotation of pinion 58 in turn rotates gear 56 and disc 50.

The disc 50 itself has an elongated rectangular orifice 64 formed therein essentially from one radial edge and extending radially inwardly past the center point of the disc. Adjacent the top and bottom of the orifice 64 are a pair of parallel rails 66 and 68 on which a masking cover 70, which is U-shaped in cross section, is slidably positioned. Thus, by moving the masking cover 70 along the rails, more or less of the orifice 64 is exposed to thereby allow more or less laser light to pass therethrough and onto the cornea. Clearly, the larger the orifice, the larger the width of the annular ablated portion 42 will be. By rotating the disc, the orifice 64 also rotates and thus the annular ablated portion 42 is formed.

Embodiment of FIG. 14

Referring now to FIG. 14, a modified guiding mechanism 72 is shown which is similar to guiding mechanism 26 shown in FIGS. 11–13 except that the size of the orifice is not variable. Thus, the modified guiding mechanism 72 is comprised of a ring 74 on a stand 76, an opaque disc 78 which is rotatable in the ring via a suitable motor, not shown, and a slidable masking cover 80. Disc 78 has a rectangular orifice 82 extending diametrically there across with parallel rails 84 and 86 on top and bottom for slidably receiving the masking cover 80 thereon, this cover being U-shaped for engagement with the rails. The masking cover 80 has its own orifice 88 therein which aligns with orifice 82 on the disc. Thus, by sliding the masking cover 80 along the rails of the disc, the location of the intersection of orifice 88 and orifice 82 can be varied to vary the radial position of the overall through orifice formed by the combination of these two orifices. As in guiding mechanism 26, the masking cover 80 and disc 78 are otherwise opaque to laser light except for the orifices.

Figure 15:
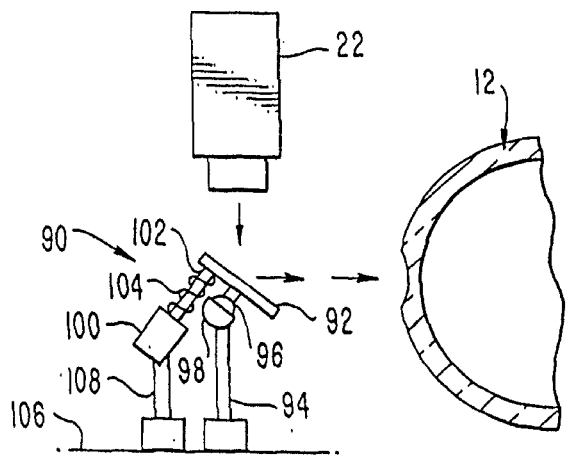
FIG. 15 is a diagrammatic side elevational view of a second modified guiding mechanism for a laser beam including a universally supported mirror and actuating motors used for moving the mirror and thereby guiding the laser beam in the predetermined pattern.

Embodiment of FIG. 15

Referring now to FIG. 15, a second modified guiding mechanism 90 is shown for directing laser light from laser beam source 22 to the cornea 12 along the desired predetermined pattern. This guiding mechanism 90 comprises a mirror 92 universally supported on a stand 94 via, for example, a ball 96 and socket 98 joint. This mirror 92 can be pivoted relative to the stand through the universal joint by means of any suitable devices, such as two small piezoelectric motors which engage the mirror at 90° intervals. For example, such a piezoelectric motor 100 having a plunger 102 coupled thereto and engaging the rear of the mirror can be utilized with a spring 104 surrounding the plunger and maintaining the mirror in a null position. The motor 100 is rigidly coupled to a base 106 via a stand 108. The second piezoelectric motor, not shown, can be located so that its plunger engages the rear of the mirror 90° from the location of motor 100. By using these two motors, springs and plungers, the mirror 92 can be fully rotated in its universal joint to direct the laser beam from source 22 onto the cornea 12 to ablate the cornea in a predetermined pattern.

Figure 16:
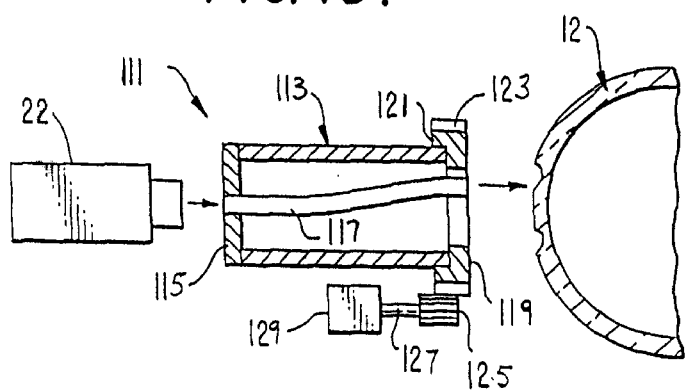
FIG. 16 is a diagrammatic side elevational view of a third modified guiding mechanism comprising a housing and a rotatable fiber optic cable.
Figure 17:
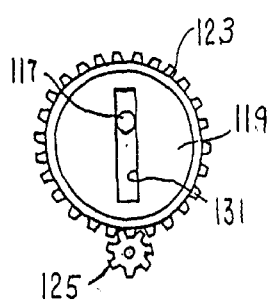
FIG. 17 is an end elevational view of the housing and fiber optic cable shown in FIG. 16.

Embodiment of FIGS. 16-17

Referring now to FIGS. 16 and 17, a third modified guiding mechanism 111 is shown for ablating a cornea 12 via directing laser light from laser source 22. This modified guiding mechanism 111 basically comprises a cylindrical housing 113 having an opaque first end 115 rotatably receiving the end of a fiber optic cable 117 therein. The second end 119 of the housing comprises a rotatable opaque disc having a flange 121 engaging the housing and an external gear 123 which in turn engages pinion 125, which is driven via shaft 127 and motor 129. Thus, rotation of the pinion results in rotation of gear 123 and thus the opaque second end 119 of the housing. This second end 119 has a diametrically oriented rectangular orifice 131 therein which receives the other end of the fiber optic cable 117 therein. That end of the fiber optic cable is either dimensioned so that it fits fairly tightly into the orifice or there is an additional suitable assembly utilized for maintaining the fiber optic cable end in a predetermined position in the orifice during rotation of the second end. However, this end would be movable radially of the orifice to change the position of the annular ablated portion formed by utilizing this guiding mechanism.

Embodiment of FIG. 18

Referring now to FIG. 18, rather than ablating the exposed internal surface 20 on the cornea 12, the inner surface 133 of the removed thin corneal layer 18 can be ablated utilizing the apparatus shown in FIG. 18. Likewise, the apparatus of FIG. 18 can be used on an eye bank cornea removed from the eye and then positioned in the patient's eye to modify the curvature of the patient's combined corneal structure. This apparatus as before includes the source of the laser light 22, an adjustable diaphragm 24, and a guiding mechanism 26. In addition, an assembly 134 is utilized to support the rather flimsy removed thin corneal layer. This assembly 134 comprises a pair of laser light transparent cups 136 and 138 that are joined together in a sealing relationship via clamps 140 and engage therebetween the outer periphery of the thin corneal layer 18. Each of the cups has an inlet pipe 142, 144 for injecting pressurized air or suitable fluid into each via pumps 146 and 148. By using this pressurized container, the thin corneal layer 18 is maintained in the desired curvature so that the laser beam can provide a precise ablated predetermined pattern therein. In order to maintain the curvature shown in FIG. 18, the pressure on the right hand side of the thin layer is slightly greater than that on the left hand side.

Once the thin corneal layer 18 is suitably ablated as desired, it is replaced on the exposed internal surface 20 of the cornea and varies the curvature of the overall cornea as described above and illustrated in FIGS. 4–9.

Embodiment of FIGS. 19–27

Referring now to FIGS. 19–27, a patient's live in situ eye 110 is shown for the treatment of myopia in accordance with the present invention. Eye 110 includes a cornea 112, a pupil 114, and a lens 116, and is treated in accordance with the present invention without freezing the cornea.

Correction of myopia can be achieved by decreasing the curvature of the outer surface of cornea 112 (i.e., flattening the central portion of the cornea). This is accomplished by first cutting an incision 118 into the epithelium of cornea 112. Incision 118 may be curved or straight, and is preferably about 2.0–3.0 mm long and about 3.0–6.0 mm away from the center of cornea 112. A laser or spatula (i.e., a double-edge knife) may be used to make incision 118 in cornea 112.

Figure 19:
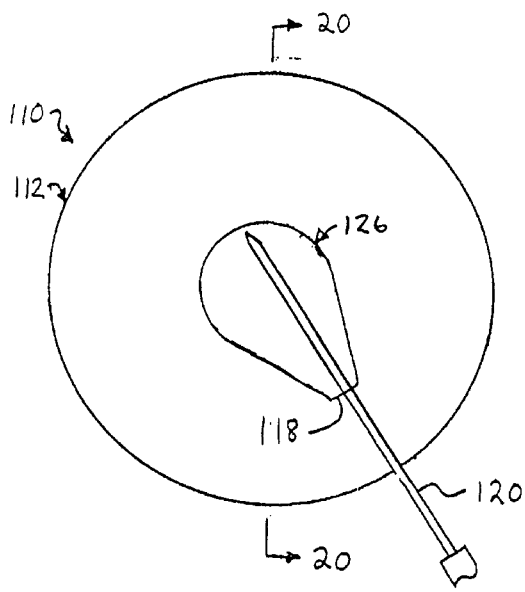
FIG. 19 is a front elevational view of a live cornea which has been cut with a spatula to separate the central portion of the cornea into first and second opposed internal surfaces in accordance with the present invention.
Figure 20:
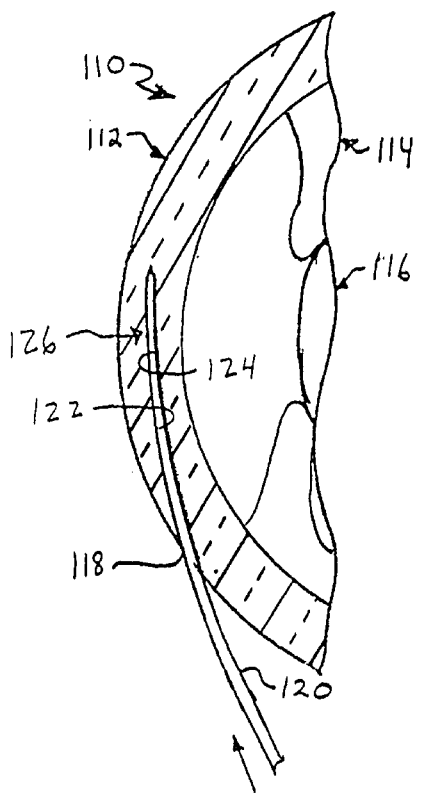
FIG. 20 is a side elevational view in section taken along line 20—20 of the cornea shown in FIG. 19.

As seen in FIGS. 19 and 20, once incision 118 is made, a spatula 120 is inserted into incision 118 to separate an internal area of live cornea 112 into first and second opposed internal surfaces 122 and 124, thereby creating an intrastromal or internal pocket 126. First internal surface 122 faces in the posterior direction of eye 110, while second internal surface 124 faces in the anterior direction of eye 110, and both of these surfaces extend radially relative to the center of the cornea.

As seen in FIGS. 19 and 20, pocket 126 is created by moving spatula 120 back and forth within an intrastromal area of cornea 112. It is important when creating pocket 126 to keep spatula 120 in substantially a single plane and substantially tangential to the cornea's internal surfaces to prevent intersecting and rupturing the descemet or Bowman's membrane.

Preferably, spatula 120 is about 3.0–12.0 mm long with a thickness of about 0.1–1.0 mm, and a width of about 0.1–1.2 mm. Spatula 120 may be slightly curved, as seen in FIG. 20, or may be straight.

While a spatula 120 is shown in FIGS. 19 and 20 for separating the internal surfaces of cornea 112, a fiber optic cable coupled to a laser beam source may be used instead of spatula 120 to separate cornea 112 into first and second opposed internal surfaces 122 and 124.

Figure 21:
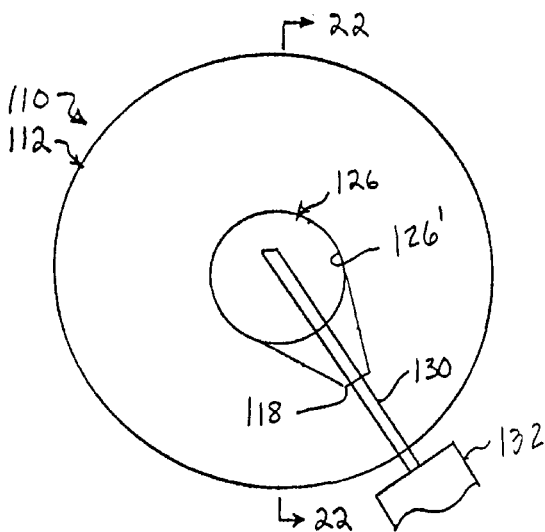
FIG. 21 is a front elevational view of a cornea that has been cut as shown in FIG. 19 with ablation conducted in the central portion of the cornea by a laser.
Figure 22:
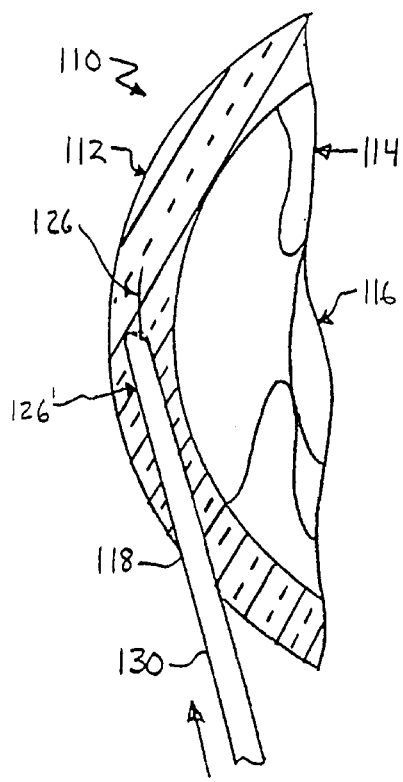
FIG. 22 is a side elevational view in section taken along line 22—22 of the cornea shown in FIG. 21.

As seen in FIGS. 21 and 22, after pocket 126 is formed, a fiber optic cable tip 130 coupled to a fiber optic cable 132, which is in turn coupled to a laser, is then inserted through incision 118 and into pocket 126 for ablating a substantially circular area of cornea 112, thereby removing a substantially disc-shaped portion of cornea 112 to form a disc-shaped cavity 126'. The laser beam emitted from tip 130 may be directed upon either first internal surface 122, second internal surface 124, or both, and removes three-dimensional portions therefrom via ablation. The fiber optic cable can be solid or hollow as desired.

The laser source for fiber optic cable 132 is advantageously a long wavelength, infrared laser, such as a $CO_2$, an erbium or holmium laser, or a short wavelength, UV-excimer laser of the argon-fluoride or krypton-fluoride type. This type of laser will photoablate the intrastromal tissue of the cornea, i.e., decompose it without burning or coagulating.

Figure 25:
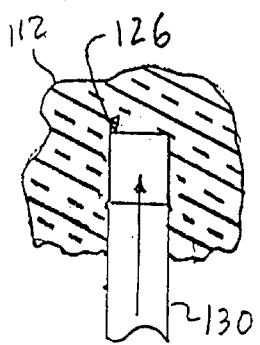
FIG. 25 is an enlarged, partial cross-sectional view of a cornea with a fiber optic tip cutting, separating and ablating the cornea into first and second opposed internal surfaces.
Figure 26:
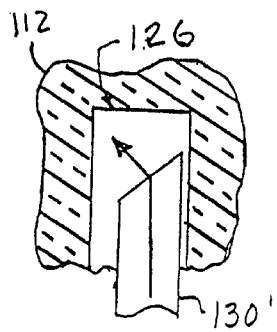
FIG. 26 is an enlarged, partial cross-sectional view of a cornea with a fiber optic tip having an angled end for ablating the cornea.
Figure 27:
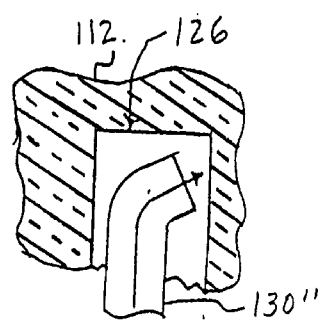
FIG. 27 is an enlarged, partial cross-sectional view of a cornea with a fiber optic tip having a bent end for ablating the cornea.
Figure 28:
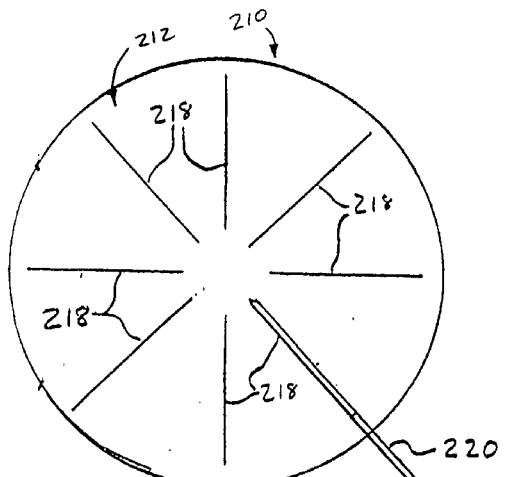
FIG. 28 is a front elevational view of a live cornea in which a plurality of radially extending cuts have been made with a spatula to separate the cornea at each of the radially extending cuts into first and second opposed internal surfaces in accordance with the present invention.
Figure 29:
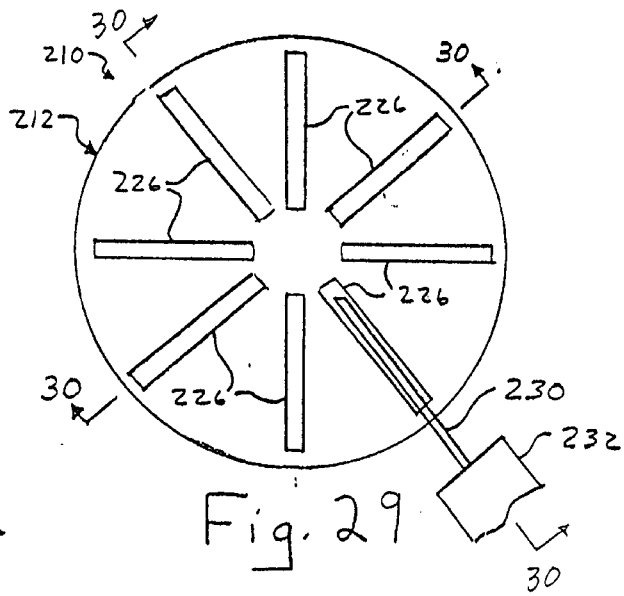
FIG. 29 is a front elevational view of a cornea in which the radially extending cuts shown in FIG. 28 have been ablated to create a plurality of radially extending tunnels.

FIGS. 25–27 illustrate three different configurations of the tip of a fiber optic cable for ablating the cornea. In FIG. 25, tip 130 has a substantially straight end for directing the laser beam parallel to the tip. As seen in FIG. 26, tip 130' has an end with an angled surface for directing the laser beam at an acute angle of preferably 45° relative to the tip to aid in ablating the cornea as desired. In FIG. 27, tip 130", has a curved end for bending the laser beam to aid ablating the cornea as desired.

Figure 23:
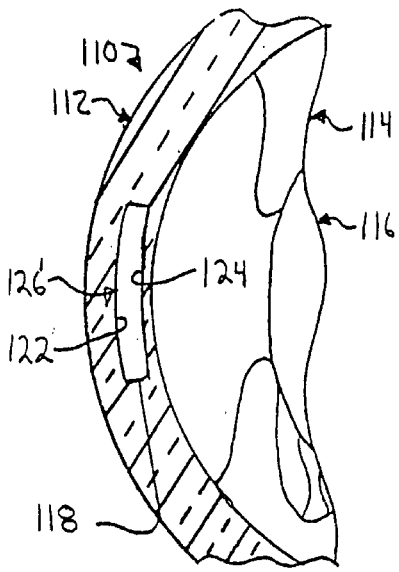
FIG. 23 is a side elevational view in section taken through the center of an eye showing the ablated cornea of FIGS. 19–22 with the fiber optic tip removed.

As seen in FIG. 23, cornea 112 is shown with the substantially disc-shaped cavity 126' formed at the center of cornea 112 just after tip 130 has been removed and prior to cornea 112 collapsing or flattening. The disc-shaped cavity 126' can be varied in size and shape, depending upon the amount of curvature modification needed to correct the patient's eyesight. Accordingly, any three-dimensional intrastromal area of the cornea may be removed to modify the cornea as desired. The intrastromal area removed can be uniform or non-uniform. For example, more material can be removed from the periphery of the cornea than from the center portion. Alternatively, more material can be removed from the center portion than from the peripheral area. The removal of peripheral portions of the cornea result in an increase of the curvature of the center portion of the cornea after the collapse of the peripheral area.

Figure 24:
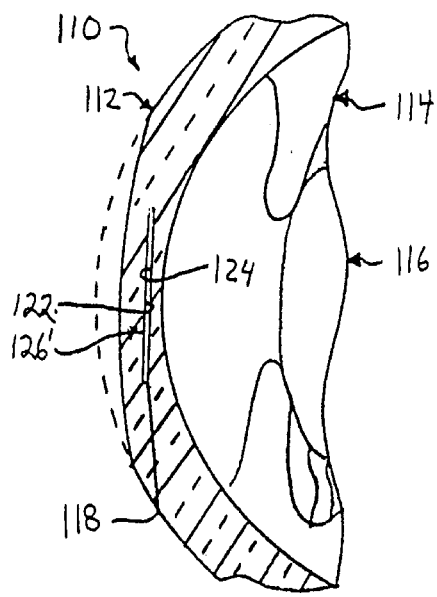
FIG. 24 is a side elevational view in section taken through the center of an eye showing the ablated cornea of FIGS. 19–23 in its collapsed position, thereby decreasing the curvature of the central portion of the cornea.

As seen in FIG. 24, after pocket 126 is ablated and tip 130 removed, the ablated cavity 126' then collapses under normal eye pressure to recombine ablated first and second internal surfaces 122 and 124 together. This collapsing and recombining of the intrastromal area of the cornea decreases the curvature of the central portion of cornea 112 from its original shape shown in broken lines to its new shape as seen in FIG. 24. After a period of time, depending on the patient's healing abilities, the ablated surfaces heal and grow back together, resulting in a permanent modification of the cornea's curvature.

Embodiment of FIGS. 28–31

Referring now to FIGS. 28–31, an eye 210 is shown for the treatment of myopia in accordance with another embodiment of the present invention, and includes a cornea 212, a pupil 214, and a lens 216, the cornea being treated without freezing it. In this embodiment, correction of myopia is accomplished by first making a plurality of radially directed intrastromal incisions 218 with a flat pin or blade spatula 220. These incisions 218 separate the cornea 218 into first and second opposed internal surfaces 222 and 224 at each of the incisions 218. First internal surfaces 222 face in the posterior direction of eye 210, while second internal surfaces 224 face in the anterior direction of eye 210, and both extend radially relative to the center of the cornea. Spatula 220 may have a straight or curved blade with a maximum diameter of about 0.1–0.2 mm. A laser may be used instead of spatula 220 to make incisions 218, if desired.

Incisions or unablated tunnels 218 extend generally radially towards the center of cornea 212 from its periphery. Preferably, incisions 218 stop about 3.0 mm from the center of cornea 212, although incisions 218 may extend to the center of cornea 212, depending upon the degree of myopia. Incisions 218 will normally extend about 3.0–10.0 mm in length, again depending on the amount of change desired in curvature of cornea 112. While only radial incisions have been shown, it will be apparent to those skilled in the art that the incisions may be non-radial, curved, or other shapes. When creating incisions 218, it is important to keep the spatula 220 in substantially a single plane so as not to intersect and puncture the descemet or Bowman's membrane.

Once intrastromal incisions 218 have been created with spatula 220, a fiber optic cable tip 230 coupled to a fiber optic cable 232 and a laser is then inserted into each of the incisions 218 for ablating tunnels 226 to the desired size. The laser beam emitted from tip 230 may be directed upon either first internal surface 222, second internal surface 224, or both for ablating tunnels 226 and removing three-dimensional portions from these surfaces.

The laser source for cable 232 is advantageously similar to the laser source for cable 132 discussed above.

Figure 30:
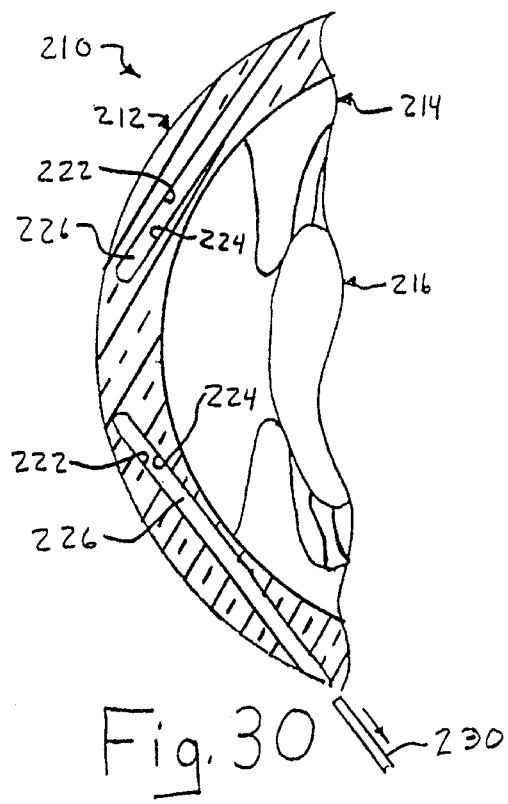
FIG. 30 is a side elevational view in section taken along line 30—30 of the cornea of FIG. 29 with the fiber optic tip removed.
Figure 31:
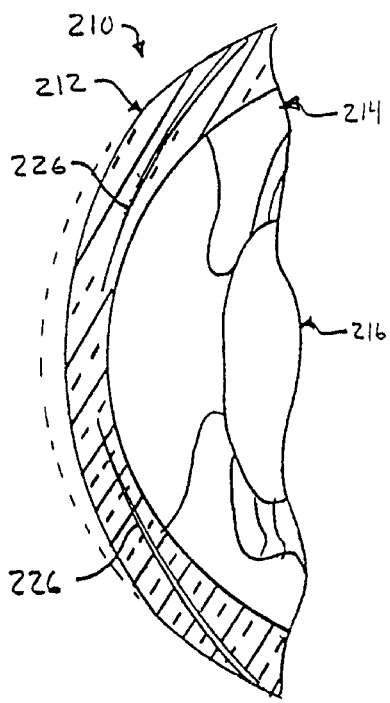
FIG. 31 is a side elevational view in section taken along the center of an eye showing the ablated cornea of FIGS. 28–30 in its collapsed position, thereby decreasing the curvature of the central portion of the cornea.

Referring now to FIGS. 30 and 31, a pair of ablated tunnels 226 are shown. In FIG. 30, cornea 212 is shown with ablated tunnels 226 just after tip 230 has been removed and prior to tunnels 226 collapsing or flattening. In FIG. 31, cornea 212 is shown after ablated tunnels 226 have collapsed to recombine first and second internal surfaces 222 and 224, thereby flattening cornea 212. In other words, this collapsing and recombining of the intrastromal area of the cornea decreases the curvature of the central portion of cornea 212 from its original shape shown in broken lines to its new shape as seen in FIG. 31. By collapsing intrastromal tunnels, this allows the outer surface of the cornea to relax, i.e., decrease surface tension, thereby permitting flattening of the cornea.

Embodiment of FIGS. 32–35

Referring now to FIGS. 32–35, an eye 310 is shown for the treatment of hyperopia in accordance with another embodiment of the present invention. Eye 310 includes a cornea 312, a pupil 314, and a lens 316. Correction of hyperopia can be achieved by increasing the curvature of the outer surface of cornea 312 (i.e., making the central portion of the cornea more curved), without freezing the cornea.

This is accomplished by making a plurality of intrastromal incisions or tunnels 318 with a spatula 320 to form first and second opposed internal surfaces 322 and 324. Tunnels 318 extend substantially radially towards the center of cornea 312. While eight equally spaced, radial tunnels 318 are shown, it will be apparent to those skilled in the art that more or fewer tunnels with varying distances apart may be made, depending upon the amount of curvature modification needed.

The initial step of making incisions or tunnels 318 of FIGS. 32–35 is similar to the initial step of making incisions 218 of FIGS. 28–31. Accordingly, spatula 320 is similar to spatula 220 discussed above. Likewise, a laser may be used to make incisions or tunnels 318 instead of spatula 320.

Once tunnels 318 are created, a fiber optic cable tip 330 extending from fiber optic cable 332 is inserted into each tunnel 318 to direct a laser beam on either first internal surface 322, second internal surface 324, or both internal surfaces to coagulate an intrastromal portion of cornea 312. As seen in FIG. 34, a point 326 at the end of each of the tunnels 318 is coagulated. Preferably, coagulation points 326 lie substantially on the circumference of a circle concentric with the center of cornea 312. The size of the circle forming coagulation points 326 depends upon the amount of curvature modification needed. Likewise, the number of coagulation points and their positions in the cornea depend upon the desired curvature modification needed.

Coagulating intrastromal points of the cornea 312, such as coagulation points 326, with a laser causes those points of the cornea, and especially the collagen therein, to heat up and shrink. This localized shrinkage of the intrastromal portion of the cornea causes the outer surface of the cornea to be tightened or pulled in a posterior direction at each of the coagulation points, and thereby causes an increase in the overall curvature of the cornea as seen in FIG. 35. Coagulation, rather than ablation, is accomplished by using a laser having a wavelength which essentially cooks the corneal tissue and which is between the wavelengths associated with long infrared light and short ultraviolet light.

Embodiment of FIG. 36

As seen in FIG. 36, rather than using a laser to remove corneal tissue in the cavities 126 formed in the cornea 112 or to form those cavities, a rotating drill tip 400 suitably coupled to a rotary or oscillating power source can be used to ablate the tissue by cutting. Likewise, any other suitable mechanical device can be used to remove the corneal tissue or form the cavities. A suitable evacuation device, such as a vacuum tube, can also be used to aid in evacuating from the cavity the tissue removed from the cornea.

Embodiment of FIGS. 37–45 Referring now to FIGS. 37–45, a patient's live in situ eye 410 is shown for the treatment of hyperopia or myopia and/or improving a patient's vision by removing opaque portions of the cornea in accordance with the present invention. The eye 410 of FIGS. 37–40 and 43–45 includes a cornea 412, a pupil 414 and a lens 416, and is treated in accordance with the present invention without freezing any portion of cornea 412.

Figure 37:
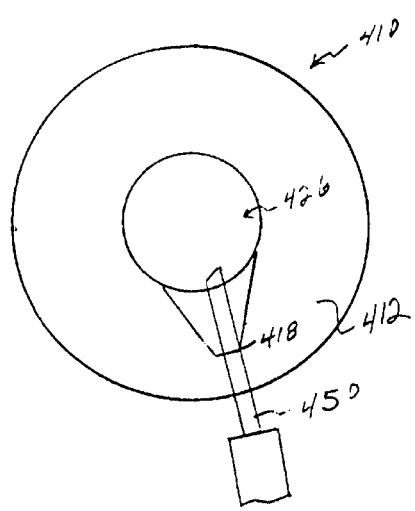
FIG. 37 is a front elevational view of a live cornea that has been cut to form an intrastromal pocket and showing a tool for injecting or implanting ocular material into the pocket.

Correction of myopia and hyperopia can be achieved by modifying the curvature of the outer surface of cornea 412, i.e., flattening the central portion of a cornea in the case of myopia or increasing the curvature in the case of hyperopia. This is accomplished by first cutting an incision 418 into the epithelium of cornea 412 as seen in FIG. 37. Incision 418 may be curved or straight, and is preferably about 2.0–3.0 mm long and about 3.0–6.0 mm away from the center of cornea 412. A laser or a double-edge knife may be used to make incision 418 in cornea 412.

As seen in FIGS. 37–40 and 43–45, once incision 418 is made, a spatula or laser probe is inserted into incision 418 to separate an internal area of live cornea 412 into first and second opposed internal surfaces 422 and 424, thereby creating an intrastromal or internal pocket 426 as in the previous embodiment of FIGS. 19–27. First internal surface 422 faces in the posterior direction of eye 410, while second internal surface 424 faces in the anterior direction of eye 410, and both of these surfaces extend radially relative to the center of the cornea 412.

Pocket 426 can have corneal tissue removed from either or both of internal surfaces 422 and 424. In other words, internal surfaces 422 and 424 of intrastromal pocket 426 can be ablated or cut to define a cavity. The ablating or removing of the internal surfaces 422 and 424 of cornea 412 is particularly desirable to remove opaque areas of cornea 412. Alternatively, the internal surfaces 422 and 424 of cornea 412 can be removed by a scalpel or a diamond tipped drill similar to the embodiments discussed above. Pocket 426 can be created by substantially the same method as previously discussed. Of course, incision 418 and pocket 426 can be made in one single step by a laser or a cutting mechanism. Alternatively, none of the corneal tissue can be removed from internal surfaces 422 and 424.

Figure 38:
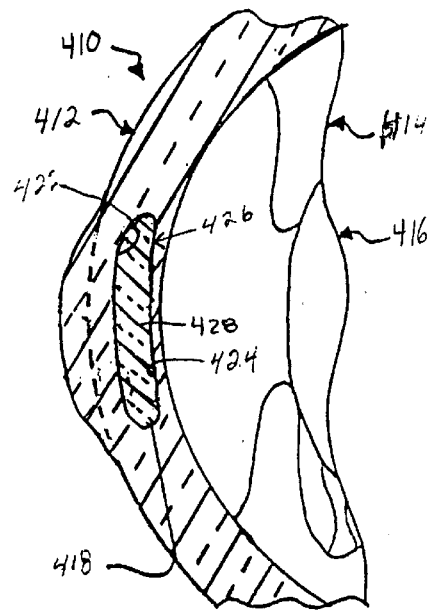
FIG. 38 is an enlarged side elevational view in section taken through the center of an eye showing the intrastromal pocket over filled with ocular material thereby increasing the curvature of the central portion of the cornea.
Figure 39:
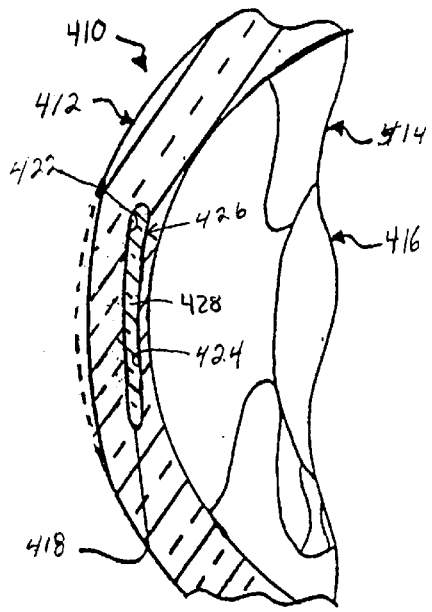
FIG. 39 is an enlarged side elevational view in section taken through the center of an eye showing the intrastromal pocket partially filled with ocular material thereby decreasing the curvature of the central portion of the cornea.
Figure 40:
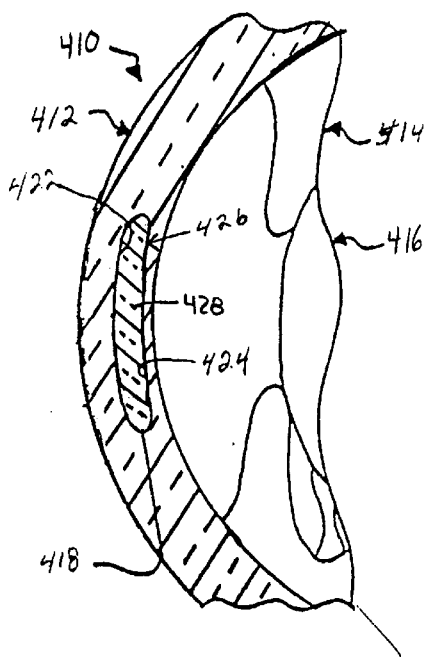
FIG. 40 is an enlarged side elevational view in section taken through the center of an eye showing the intrastromal pocket completely filled with ocular material restoring the curvature of the central portion of the cornea to its original curvature.

As shown in FIGS. 37–40 and 43–45, once the pocket 426 is formed, an ocular material 428 or 430 is inserted into pocket 426 by a tool 450. Ocular material 428 or 430 as used herein refers to transparent fluids or solids or any combination thereof. In the examples of FIGS. 38–40, the ocular material is a gel or fluid type material 428, which can be injected into pocket 426 via tool 450. In other words, in the examples of FIGS. 38–40, tool 450 is a needle for injecting ocular material 428 into pocket 426. In examples of FIGS. 43–45, the ocular material is a flexible, resilient ring shaped member 430.

In either case, ocular material 428 or 430 can have either the same refractive index as the intrastromal tissue of cornea 412 or a different refractive index from the intrastromal tissue of cornea 412. Thus, the vision of the patient can be modified by curvature modification and/or by changing the refractive index. Moreover, the patient's vision can be modified by merely removing opaque portions of the cornea and replacing them with ocular material with a refractive index the same as the intrastromal tissue of cornea 412.

In the examples of FIGS. 38–40 using ocular material 428, pocket 426 can be overfilled, partially filled, or completely filled to modify the cornea as needed. The cavity or pocket 426 can be filled completely with the ocular material to restore the normal curvature of cornea 426 as seen in FIG. 40. The amount of ocular material introduced to pocket 426 can be increased to increase the curvature of the cornea from the original curvature to treat hyperopia as seen in FIG. 38. Alternatively, the amount of the ocular material introduced to pocket 426 can be reduced to decrease the curvature or flatten cornea 412 from the original curvature to treat myopia as seen in FIG. 39. This method is suitable for correctly vision of 12 diopters or more. After the pocket 426 is filled, the internal surfaces 422 and 424 of pocket 426 come together to encapsulate ocular material 428 within cornea 412. The surfaces heal and grow back together, resulting in a permanent modification of the cornea's curvature.

The ocular material 428 injected into pocket 426 can be any suitable material that is bio-compatible and does not visually interfere with the patient's eyesight. Preferably, the ocular material 428 of FIGS. 38–40 is a transparent gellable collagen such as gelatin in an injectable form which is available from various commercial sources as known in the art. Generally, the collagen to be used in the present invention is a type I collagen. Of course, ocular material 428 can be a transparent or translucent bio-compatible polymer gel such as a silicone gel or an injectable polymethylmethacrylate. Preferably, ocular material 428 is a polymeric material that is transparent, flexible, and hydrophilic. It will be understood by those skilled in the art from this disclosure that ocular material 428 can be any suitable polymeric material. Of course, ocular material 428 can be a flexible solid or semi-solid material as shown in the examples of FIGS. 41–45 discussed below regarding ocular material 430 which can be made from collagen or synthetic polymers such as acrylic polymers, silicones and polymethylmethacrylates.

Referring now to the examples of FIGS. 43–45 using a solid or semi-solid ocular material or implant 430, tool 450 is utilized to insert ocular material or implant 430 through the small opening formed by incision 418 in the external surface of cornea 412, as seen in FIG. 37 so that ocular material or implant 430 can be implanted into pocket 426 and centered about the main optical axis of eye 410. Ocular material or implant 430 is preferably a resilient, flexible member, which can be folded for insertion into pocket 426 through the small opening formed by incision 418.

The ocular implant 430 is made from a bio-compatible transparent material. Preferably, ocular implant 430 is made from any suitable transparent polymeric material. Suitable materials include, for example, collagen, silicone, polymethylmethacrylate, acrylic polymers, copolymers of methyl methacrylate with siloxanylalkyl methylacrylates, cellulose acetate butyrate and the like. Such materials are commercially available from contact lens manufacturers. For example, optical grade silicones are available from Allergan, Alcon, Staar, Chiron and Iolab. Optical grade acrylics are available from Allergan and Alcon. A hydrogel lens material consisting of a hydrogel optic and polymethylmethacrylate is available from Staar.

Similar to the fluid type ocular material 428, discussed above, solid or semi-solid ocular material or implant 430 can overfill, partial fill or completely fill pocket 426 to modify cornea 412 as needed. While ablation or removal of intrastromal tissue of pocket 426 is required for decreasing the curvature of cornea 412 as seen in FIG. 44, or for maintaining the original curvature of cornea 412 as seen in FIG. 45, such ablation or removal of intrastromal tissue of pocket 426 is not necessary for increasing the curvature of cornea 412. In any event, the amount of intrastromal tissue to be removed, if any, from pocket 426 depends on the shape of ocular material 430 and the desired resultant shape of cornea 412.

As seen in FIGS. 41 and 42, ocular material or implant 430 has a substantially annular ring shape with a center opening or circular hole 432. Center opening 432 allows intrastromal fluids to pass through ocular material or implant 430. Preferably, ocular material 430 has a circular periphery with an outer diameter in the range of about 3.0 mm to about 9.0 mm. Center opening 432 preferably ranges from about 1.0 mm to about 8.0 mm. The thickness of ocular material 430 is preferably about 20 microns to about 1000 microns. It should be apparent from this disclosure that ocular material 430 can be a partial ring or a full ring with a slit. Moreover, ocular material 430 can be an oval ring.

In the embodiment of FIGS. 41–45, ocular material or implant 430 has a planar face 434 and a curved face 436. Planar face 434 forms a frustoconically shaped surface, which faces inwardly towards the center of eye 410 in a posterior direction of eye to contact internal surface 424 of pocket 426. Curved face 436 can be shaped to form a corrective lens or shaped to modify the curvature cornea 412 as seen in FIGS. 43 and 44. Of course, ocular material 430 can be shaped to replace opaque areas of cornea 412, which have been previously removed, and/or to form a corrective lens without changing the curvature of cornea 412 as seen in FIG. 45.

When center opening 432 is about 2.0 mm or smaller, center opening 432 acts as a pin hole such that the light passing through is always properly focused. Accordingly, ocular material 430 with such a small center opening 432 can be a corrective lens, which is not severely affected by center opening 432. However, when ocular material 430 has its center opening 432 greater than about 2.0 mm, then ocular material 430 most likely will have the same refractive index as the intrastromal tissue of cornea 412 for modifying the shape of cornea 412 and/or replacing opaque areas of the intrastromal tissue of cornea 412. Of course, all or portions of ocular material 430 can have a refractive index different from the intrastromal tissue of cornea 412 to correct astigmatisms or the like, when center opening 432 is greater than about 2.0 mm.

The amount of curvature modification and/or the corrective power produced by ocular material 430 can be varied by changing the thickness, the shape, the outer diameter and/or the size of the center opening 432. Moreover, instead of using a continuous, uniform ring as illustrated in FIGS. 41 and 42, ocular material 430 can be a ring with non-uniform cross-section in selected areas as necessary to correct the patient's vision. In addition, ocular material 430 could be replaced with a plurality of separate solid or semi-solid ocular implants at selected locations within pocket 426 of cornea 412.

Embodiment of FIGS. 46–53

Referring now to FIGS. 46–53, an eye 510 is shown for the treatment of hyperopia or myopia and/or improving vision by removing opaque portions of the cornea, in accordance with another embodiment of the present invention. Eye 510 includes a cornea 512, a pupil 514, and a lens 516. As in the previous embodiments, cornea 512 is treated without freezing it.

In this embodiment, correction of hyperopia or myopia or removal of opaque portions can be accomplished by first making a plurality of radially directed intrastromal incisions 518 with a flat pin, laser or blade spatula similar to the procedure mentioned above discussing the embodiment of FIGS. 28–31. These incisions 518 separate cornea 512 into first and second opposed internal surfaces 522 and 524, respectively, at each of the incisions 518. First internal surfaces 522 face in the posterior direction of eye 510, while second internal surfaces 524 face in the anterior direction of eye 510, and both extend radially relative to the center of cornea 512.

Incisions or unablated tunnels 518 extend generally radially towards the center of cornea 512 from its periphery. Preferably, incisions 518 stop about 3.0 mm from the center of cornea 512, although incisions 518 may extend to the center of cornea 512, depending upon the degree of hyperopia or myopia. Incisions 518 will normally extend about 3.0–10.0 mm in length, again depending on the amount of change desired in curvature of cornea 512. While only radial incisions have been shown, it will be apparent to those skilled in the art that the incisions may be non-radial, curved, or other shapes. When creating incisions 518, it is important to keep the spatula or laser in substantially a single plane so as not to intersect and puncture the descemet or Bowman's membrane.

Once intrastromal incisions 518 have been created, a fiber optic cable tip coupled to a fiber optic cable and a laser can be optionally inserted into each of the incisions 518 for ablating tunnels 526 to the desired size, if needed or desired. The laser beam emitted from the tip may be directed upon either first internal surface 522, second internal surface 524, or both for ablating tunnels 526 to sequentially and incrementally remove three-dimensional portions from these surfaces. The laser source for the cable is advantageously similar to the laser source for the cable as discussed above. Alternatively, a drill or other suitable micro-cutting instruments can be used to sequentially and incrementally remove portions of the cornea.

Figure 46:
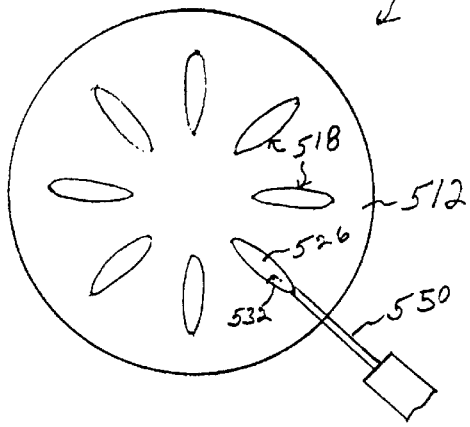
FIG. 46 is a front elevational view of a live cornea which has been cut to form a plurality of radial tunnels or pockets and showing a tool for injecting or implanting ocular material into the tunnels.

Referring to FIG. 46, a plurality of radial tunnels 526 are shown with a suitable tool 550 projecting into one of the tunnels 526 for introducing optical material 528 into tunnels 526 to modify cornea 512. Ocular material 528 as used herein refers to transparent fluids or solids or any combination thereof. In the examples of FIGS. 47–53, ocular material 528 is a gel or fluid type material, which can be injected into pockets 526 via tool 550. Preferably, in this case, tool 550 is a needle for injecting ocular material 528 into pockets 526. Of course as in the preceding embodiment, a solid implant or ocular material may be introduced into pockets 526. Also, ocular material 528 can have either a refractive index, which is different or the same as the intrastromal tissue of cornea 512 as needed and/or desired, whether the ocular material is a gel, a solid or any combination thereof.

Figure 47:
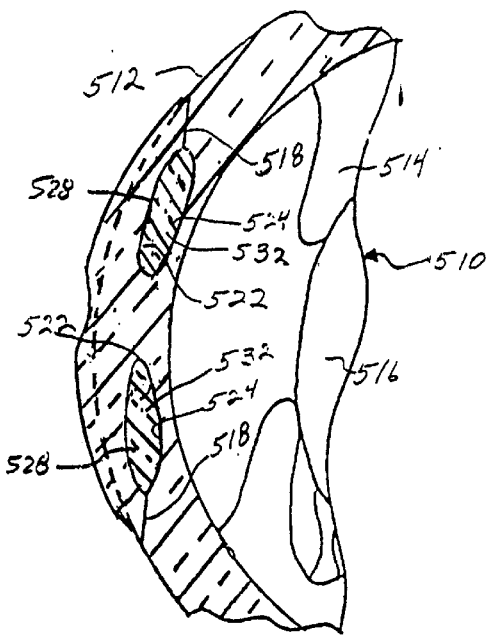
FIG. 47 is an enlarged side elevational view in section taken through the center of the eye showing the radial tunnels or pockets of FIG. 46 overfilled with ocular material thereby modifying the cornea and increasing its curvature.

As shown in FIG. 47, optical material 528 injected into the ablated tunnels 526 expands the outer surface of cornea 512 outward to change or modify the curvature of the central portion of cornea 512 from its original shape shown in broken lines to its new shape shown in full lines.

Figure 48:
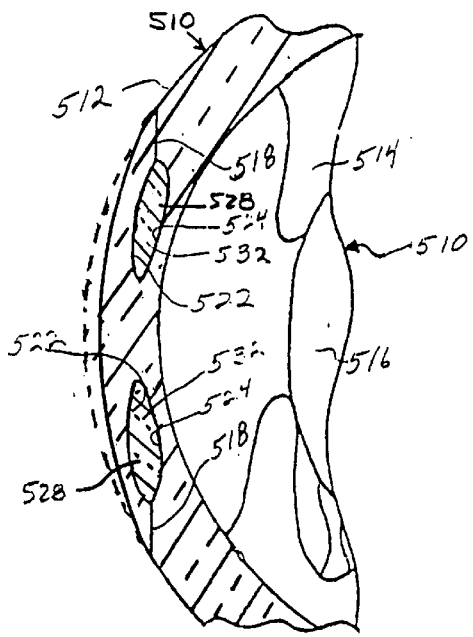
FIG. 48 is an enlarged side elevational view in section taken through the center of the eye showing the radial tunnels or pockets of FIG. 46 underfilled with ocular material thereby modifying the cornea and decreasing its curvature.
Figure 49:
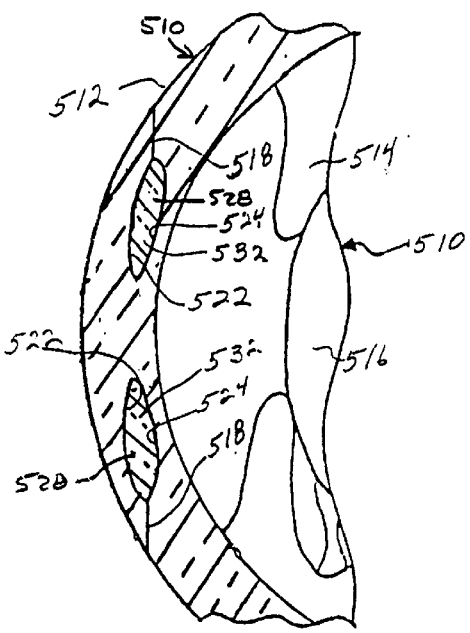
FIG. 49 is an enlarged side elevational view in section taken through the center of the eye showing the radial tunnels or pockets of FIG. 46 completely filled with ocular material thereby modifying the cornea.

As seen in FIGS. 47–53, the various radial tunnels 526 can be filled with ocular material 528 to overfill pockets 526 (FIG. 47), underfill pockets 526 (FIG. 48) or completely fill pockets 526 (FIG. 49). Thus, by introducing various amounts of optical material into pockets 526, the curvature of cornea 512 can be varied at different areas. Similarly, selected tunnels 526 can be overfilled or completely filled at selected areas, while other selected tunnels can be partially filled, completely filled or unfilled to collapse or decrease the curvature of cornea 512 at other selected areas as shown in FIGS. 50–53. The selective alteration of the curvature in different areas of the cornea are particularly desirable in correcting astigmatisms.

In the embodiment illustrated in FIGS. 47–53, the intrastromal areas of tunnels 526 are preferably ablated by a laser or cut by a micro-cutting instrument for sequentially and incrementally removing three-dimensional portions of cornea 512 to form tubular pockets from tunnels 526. However, as in the previous embodiment of FIGS. 37 and 38, the incisions 518 can be filled with ocular material without previously ablating or cutting the internal surfaces 522 and 524 of cornea 512 to expand the cornea 512 for increasing its curvature. Ablating the internal surfaces of the cornea is advantageous to remove opaque areas of the cornea which can then be filled with the ocular material.

Figure 50:
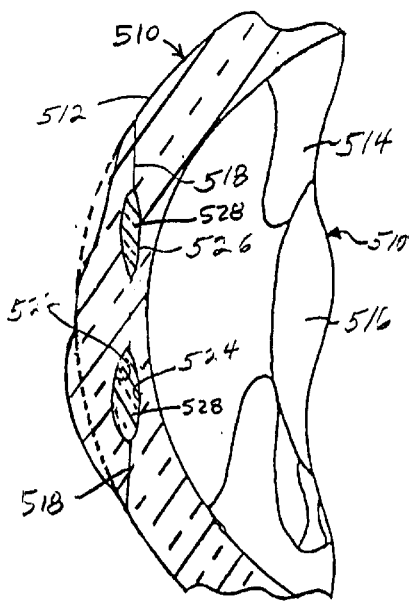
FIG. 50 is an enlarged side elevational view in section taken through the center of the eye showing one of the tunnels or pockets overfilled with ocular material to increase the curvature of a selected portion of the cornea and another tunnel or pocket underfilled to decrease the curvature of a selected portion of the cornea.
Figure 51:
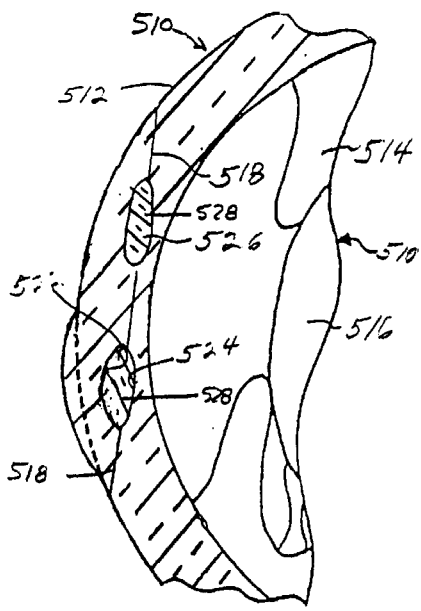
FIG. 51 is an enlarged side elevational view in section taken through the center of the eye showing one of the tunnels or pockets completely filled with ocular material to maintain a portion of the cornea at its original shape and another tunnel or pocket overfilled with ocular material to increase the curvature of a selected portion of the cornea.
Figure 52:
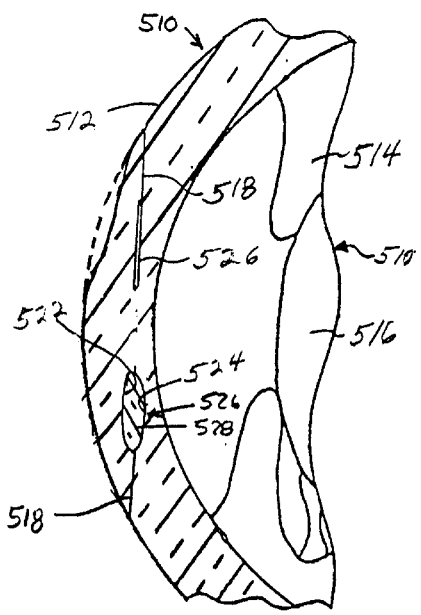
FIG. 52 is an enlarged side elevational view in section taken through the center of the eye showing one of the tunnels or pockets completely filled with ocular material to maintain a portion of the cornea at its original shape and another tunnel or pocket unfilled to collapse or decrease the curvature of a selected portion of the cornea.
Figure 53:
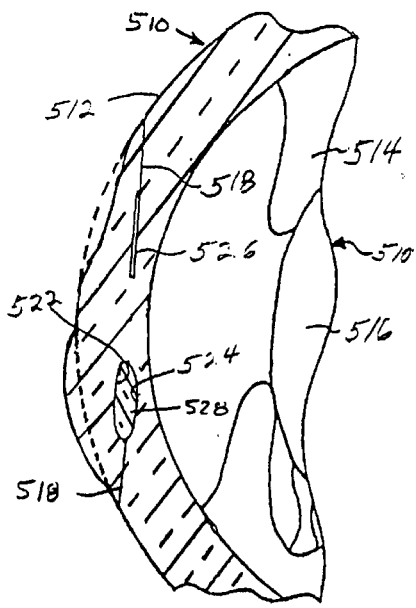
FIG. 53 is an enlarged side elevational view in section taken through the center of the eye showing one of the tunnels or pockets overfilled with ocular material to increase the curvature of a selected portion of the cornea and another tunnel or pocket unfilled to collapse or decrease the curvature of a selected portion of the cornea.

As shown in FIGS. 48 and 50, the amount of ocular material 528 introduced into the ablated areas of pockets 526 can be less then the amount of ablated material to reduce the curvature of cornea 512. Alternatively, the amount of ocular material 528 introduced into the ablated areas of pockets 526 can completely fill pockets 526 to retain the original curvature of cornea 512 as seen in FIGS. 49, 51 and 52.

Embodiment of FIGS. 54–57 Referring now to FIGS. 54–57, an eye 610 is shown for treatment of hyperopia, myopia and/or removal of opaque portions in accordance with another embodiment of the invention using an implant or ocular material 630. As shown, the eye 610 includes a cornea 612, a pupil 614 and a lens 616. As in the previous embodiments, the live eye 610 is treated without freezing cornea 612 or any part thereof.

In this embodiment, a thin layer 618 of cornea 612 is first removed from the center portion of a patient's live cornea 612 by cutting using a scalpel or laser. The thin layer 618 is typically on the order of about 0.2 mm in thickness with overall cornea being on the order of about 0.5 mm in thickness. Once the thin layer 618 is removed from cornea 612, it exposes first and second opposed internal surfaces 622 and 624. Generally, either or both of the internal surfaces 622 and/or 624 are the target of the ablation by the excimer laser. Alternatively, tissue from the internal surfaces 622 and/or 624 can be removed by a mechanical cutting mechanism, or substantially no tissue is removed from the cornea.

Figure 54:
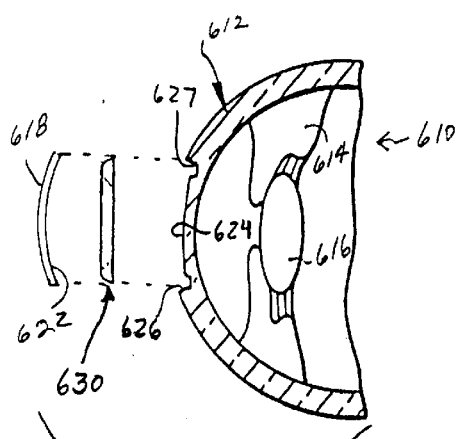
FIG. 54 is an exploded side elevational view in section taken through the center of an eye showing a thin layer or portion of the cornea completely removed from the live cornea and the ocular material or implant of FIGS. 41 and 42 positioned between the thin layer and the remainder of the live cornea.

As illustrated in FIG. 54, a disc-shaped portion 626 is removed from internal surface 624 by a laser beam or other cutting mechanism. In this embodiment, internal surface 624 is shaped to include a concave annular portion 627. The method and laser apparatus as described above in the embodiment of FIGS. 1–10 can be used for removing tissue from cornea 612 in substantially the same manner.

Figure 55:
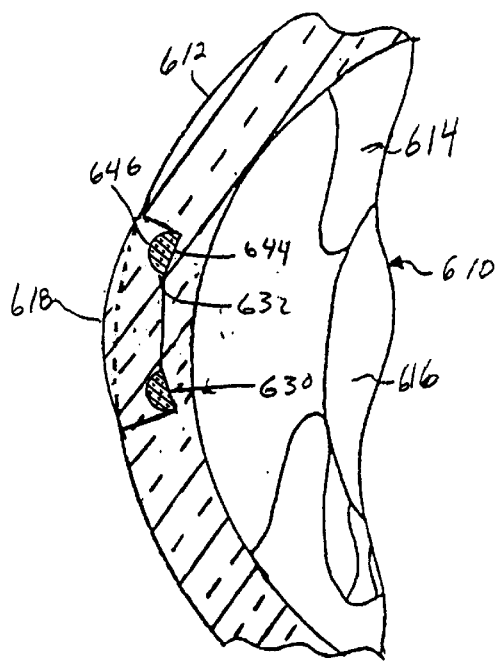
FIG. 55 is an enlarged side elevational view in section taken through the center of the eye showing the ocular implant illustrated in FIGS. 41 and 42 implanted in the cornea with the thin layer of the cornea replaced over the ocular implant to increase the curvature of the cornea.
Figure 56:
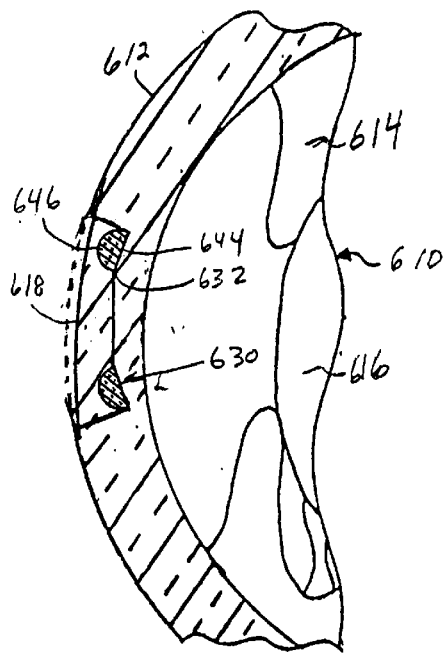
FIG. 56 is an enlarged side elevational view in section taken through the center of the eye showing the ocular implant illustrated in FIGS. 41 and 42 implanted in the cornea with the thin layer of the cornea replaced over the ocular implant to decrease the curvature of the cornea.
Figure 57:
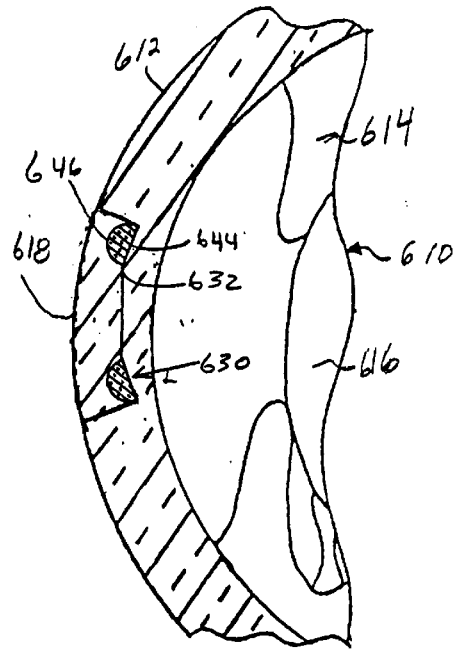
FIG. 57 is an enlarged side elevational view in section taken through the center of the eye showing the ocular implant illustrated in FIGS. 41 and 42 implanted in the cornea with the thin layer of the cornea replaced over the ocular implant to maintain the cornea's original curvature.

After the exposed internal surface 622 or 624 of cornea 612 is ablated, if necessary, an annular ring shaped implant or ocular material 630 is placed on ablated portion 628 of cornea 612. The previously removed thin layer 618 of cornea 612 is then replaced onto ablated portion 626 of cornea 612 to overlie implant or ocular material 630 and then reconnected thereto. The resulting cornea can have a modified curvature thereby modifying the refractive power of the cornea and lens system as seen in FIGS. 55 and 56, or the original curvature with opaque areas removed and/or modified refractive power as seen in FIG. 57.

The ocular implant or material 630 in the embodiment shown in FIGS. 54–57 has a substantially annular ring shape, and is substantially identical to the implant or ocular material 430 discussed above. Thus, implant 430 will not be illustrated or discussed in detail when referring to the procedures or methods of FIGS. 54–57. Similar to ocular material or implant 430, ocular material 630 can be a partial ring or a full ring with a slit.

The outer diameter of ocular implant or material 630 can be about 3–9 mm, while the inner opening 632 is generally about 1–8 mm. The thickness of ocular implant 630 is preferably about 20 to about 1000 microns. Ocular implant 630 has a planar face 644 forming a frustoconically shaped surface, which faces inwardly towards the center of eye 610 in a posterior direction of eye 610 to contact the exposed inner surface 620 of the cornea 612. The opposite face 646 is preferably a curved surface facing in an anterior direction of eye 610 as shown. The ocular implant 630 can be shaped to form a corrective lens or shaped to modify the curvature of the cornea. Similarly, the implant can be used to replace opaque areas of the cornea which have been previously removed by ablation or other means.

In the embodiment shown, ocular implant 630 preferably has a substantially uniform shape and cross-section. Alternatively, ocular implant 630 can be any suitable shape having either a uniform and/or non-uniform cross-section in selected areas as necessary to correct the patient's vision. For example, an ocular implant can be used having a circular or triangular cross section. In this manner, the curvature of a cornea can be modified at selected areas to correct various optical deficiencies, such as, for example, astigmatisms. Ocular implant 630 can be a corrective lens with the appropriate refractive index to correct the vision of the patient. The ocular implant 630 is made from a biocompatible transparent material. Preferably, ocular implant 630 is made from any suitable transparent polymeric material. Suitable materials include, for example, collagen, silicone, polymethylmethacrylate, acrylic polymers, copolymers of methyl methacrylate with siloxanylalkyl methylacrylates, cellulose acetate butyrate and the like. Such materials are commercially available from contact lens manufacturers. For example, optical grade silicones are available from Allergan, Alcon, Staar, Chiron and Iolab. Optical grade acrylics are available from Allergan and Alcon. A hydrogel lens material consisting of a hydrogel optic and polymethylmethacrylate is available from Staar.

Hydrogel ocular implant lenses can be classified according to the chemical composition of the main ingredient in the polymer network regardless of the type or amount of minor components such as cross-linking agents and other by-products or impurities in the main monomer. Hydrogel lenses can be classified as (1) 2-hydroxyethyl methacrylate lenses; (2) 2-hydroxyethyl methacrylate-N-vinyl-2-pyrrolidinone lenses; (3) hydrophilic-hydrophobic moiety copolymer lenses (the hydrophilic components is usually N-vinyl-2-pyrrolidone or glyceryl methacrylate, the hydrophobic components is usually methyl methacrylate); and (4) miscellaneous hydrogel lenses, such as lenses with hard optical centers and soft hydrophilic peripheral skirts, and two-layer lenses.

Alternatively, ocular implant 630 can be elongated or arcuate shaped, disc shaped or other shapes for modifying the shape and curvature of cornea 612 or for improving the vision of eye 610 without modifying the curvature of cornea 612. Similarly, ocular implant 630 can be placed in the intrastromal area of the cornea 612 at a selected area to modify the curvature of the cornea and correct the vision provided by the cornea and lens system. In the embodiment shown in FIGS. 54–57, thin layer 618 of cornea 612 is completely removed to expose the internal surfaces 622 and 624 of cornea 612.

Figure 58:
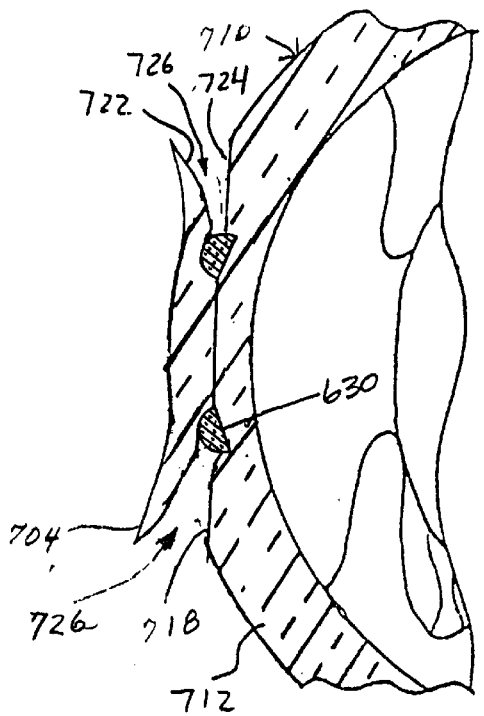
FIG. 58 is an enlarged side elevational view in cross section through the center of an eye showing a circular cut or groove in the cornea and the ocular implant of FIGS. 41 and 42 positioned between the separated internal layers, but before the separated internal layers are replaced or rejoined on the cornea.

Embodiment of FIG. 58

An alternative method of implanting ocular material or implant 630 into an eye 710 is illustrated in FIG. 58. Specifically, ocular material or implant 630 is implanted into cornea 712 of eye 710 to modify the patient's vision. In particular, this method can be utilized for the treatment of hyperopia, myopia or removal of opaque portions of the cornea. As in the previous embodiments, the treatment of eye 510 is accomplished without freezing cornea 512 or any portion thereof.

In this method, a ring or annular incision 718 is formed in cornea 712 utilizing a scalpel, laser or any cutting mechanism known in the art. The scalpel, laser or cutting mechanism can then be used to cut or ablate an annular-shaped intrastromal pocket 726 in cornea 712 as needed and/or desired. Accordingly, an annular groove is now formed for receiving ocular material or implant 630 which is discussed above in detail.

The annular groove formed by annular incision 718 separates cornea 712 into first and second opposed internal surfaces 722 and 724. First internal surface 722 faces in the posterior direction of eye 710, while second internal surface 724 faces in the anterior direction of eye 710. optionally, either internal surfaces 722 or 724 can be ablated to make the annular groove or pocket 726 larger to accommodate ocular implant 630.

The portion of cornea 712 with internal surface 722 forms an annular flap 725, which is then lifted and folded away from the remainder of cornea 712 so that ocular implant of material 630 can be placed into annular pocket 726 of cornea 712 as seen in FIG. 58. Now, corneal flap 725 can be folded over ocular implant or material 630 and reconnected to the remainder of cornea 712 via sutures or the like. Accordingly, ocular implant or material 630 is now encapsulated within cornea 712.

As in the previous embodiments, ocular implant or material 630 can modify the curvature of the exterior surface of cornea 712 so as to either increase or decrease its curvature, or maintain the curvature of the exterior surface of cornea 712 at its original curvature. In other words, ocular implant or material 630 can modify the patient's vision by changing the curvature of the cornea 712 and/or removing opaque portions of the cornea and/or by acting as a corrective lens within the cornea.

Figure 59:
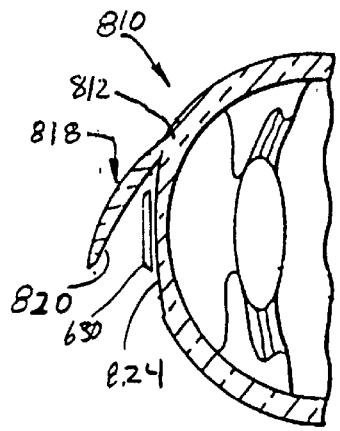
FIG. 59 is a side elevational view in section through the center of the eye showing the outer surface of the cornea cut to form a flap having a portion still attached to the cornea to expose the intrastromal layers of the cornea.

Embodiment of FIG. 59

Another embodiment of the present invention is illustrated utilizing ocular implant 630 in accordance with the present invention. More specifically, the method of FIG. 59 is substantially identical to the methods discussed above in reference to FIGS. 54–57, and thus, will not be illustrated or discussed in detail herein. Rather, the only significant difference between the methods discussed regarding FIGS. 54–57 and the method of FIG. 59 is that the thin layer 816 of FIG. 59 is not completely removed from cornea 812 of eye 810.

In other words, thin layer 818 of cornea 812 is formed by using a scalpel or laser such that a portion of layer 818 remains attached to the cornea 812 to form a corneal flap. The exposed inner surface 820 of layer 818 or the exposed internal surface 824 of the cornea can be ablated or cut with a laser or cutting mechanism as in the previous embodiments to modify the curvature of the cornea. Ocular implant 630 can then be placed between internal surfaces 820 and 824 of cornea 812. The flap or layer 818 is then placed back onto the cornea 812 and allowed to heal. Accordingly, ocular implant 630 can increase, decrease or maintain the curvature of eye 810 as needed and/or desired as well as remove opaque portions of the eye.

Figure 60:
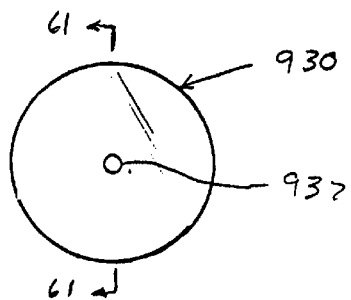
FIG. 60 is a front elevational view of an ocular implant or material in accordance with the present invention for implanting within the intrastromal area of the cornea.
Figure 61:
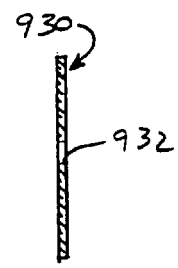
FIG. 61 is a cross-sectional view of the ocular implant or material illustrated in FIG. 60 taken along section line 61—61.

Embodiment of FIGS. 60 and 61

Referring now to FIGS. 60 and 61, an ocular implant or material 930 in accordance with the present invention is illustrated for treatment of hyperopia or myopia. In particular, ocular implant or material 930 is a disk shape member, which is as thin as paper or thinner. Ocular implant or material 930 includes a center opening 932 for allowing intrastromal fluids to pass between either sides of ocular implant or material 930. Basically, ocular implant or material 930 is constructed of a suitable transparent polymeric material utilizing diffractive technology, such as a Fresnel lens, which can be utilized to correct the focus of the light passing through the cornea by changing the refractive power of the cornea. Since ocular implant or material 930 is very thin, i.e., as thin as paper or thinner, the exterior surface of the cornea will substantially retain its original shape even after ocular implant or material 930 is inserted into the cornea. Even if there is some change in the cornea, this change can be compensated by the refractive powers of the ocular implant or material 930.

Ocular implant or material 930 can be inserted into the cornea in any of the various ways disclosed in the preceding embodiments. In particular, ocular implant or material 930 can be inserted through a relatively small opening formed in the cornea by folding the ocular implant or material 930 and then inserting it through the small opening and then allowing it to expand into a pocket formed within the intrastromal area of the cornea. Moreover, a thin layer or flap could be created for installing ocular implant or material 930 as discussed above.

The outer diameter of ocular implant or material 930 is preferably in the range of about 3.0 mm to about 9.0 mm, while center opening 932 is preferably about 1 mm to about 8.0 mm depending upon the type of vision to be corrected. In particular, ocular implant 930 can be utilized to correct hyperopia and/or myopia when using a relatively small central opening 932 such as in the range of to about 1.0 mm to about 2.0 mm. However, if the opening is greater than about 2.0 mm, then the ocular implant or material 930 is most likely designed to correct imperfections in the eye such as to correct stigmatisms. In the event of astigmatism, only certain areas of the ocular implant 930 will have a refractive index which is different from the intrastromal tissue of the cornea, while the remainder of ocular implant or material 930 has the same refractive index as the intrastromal tissue of the cornea.

Preferably, ocular implant 930 is made from a biocompatible transparent material which is resilient such that it can be folded and inserted through a small opening in the cornea and then allowed to expand back to its original shape when received within a pocket in the cornea. Examples of suitable materials include, for example, substantially the same set of materials discussed above when referring to ocular implant or material 430 or 630 discussed above.

Embodiment of FIGS. 62–73

Referring now to FIGS. 62–73, various methods in accordance with the present invention will be discussed for modifying a patient's live eye 1010 to correct the patient's vision. In particular, these methods employ many of the procedures of the prior discussed method for the treatment of hyperopia, myopia and/or improving a patient's vision by removing opaque portions of the cornea in accordance with the present invention. Accordingly, many of the prior procedures and illustrations previously mentioned herein will be used to describe the procedures of FIGS. 62–73.

As in the previous embodiments, the procedures for modifying eye 1010 of FIGS. 62–71 are accomplished by treating the intrastromal areas of cornea 1012. These procedures can include incrementally and sequentially ablating or removing three-dimensional portions of the intrastromal area of cornea 1012 and/or inserting ocular material 428, 430, 528, 630 or 930, as discussed above in the preceding embodiments.

Figure 62:
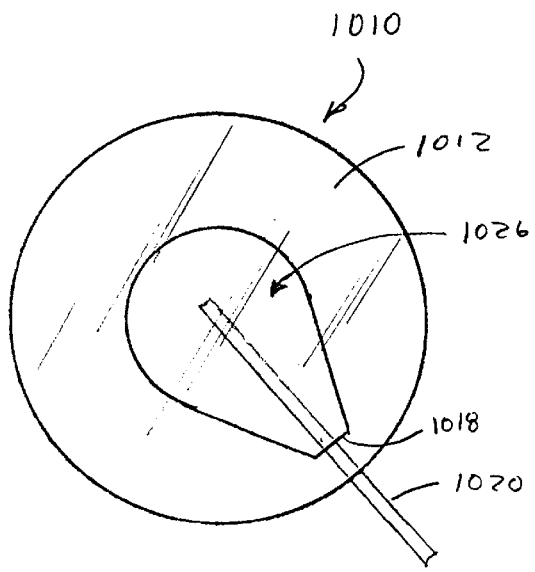
FIG. 62 is a front elevational view of the live cornea which has been cut with a tool to separate the central portion of the cornea into first and second opposed internal surfaces in accordance with the present invention.
Figure 64:
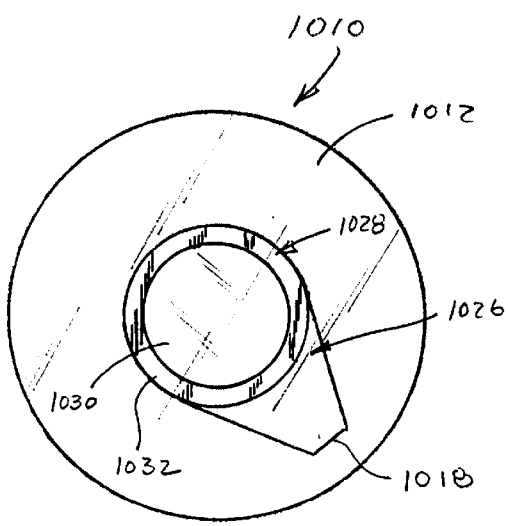
FIG. 64 is a front elevational view of the live cornea of FIG. 62 with a template inserted therein.
Figure 63:
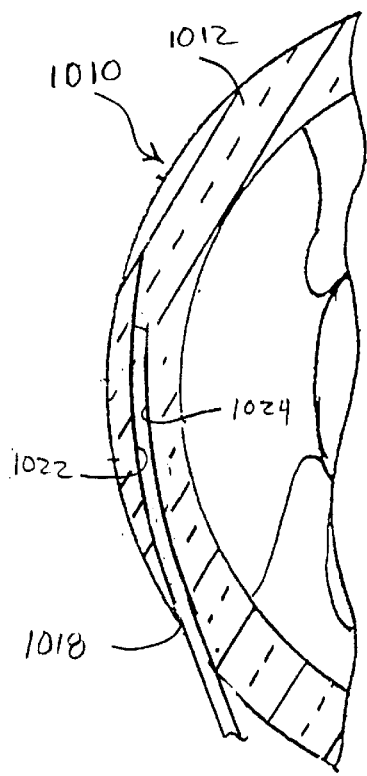
FIG. 63 is a side elevational view in longitudinal cross-section of the cornea shown in FIG. 62.
Figure 65:
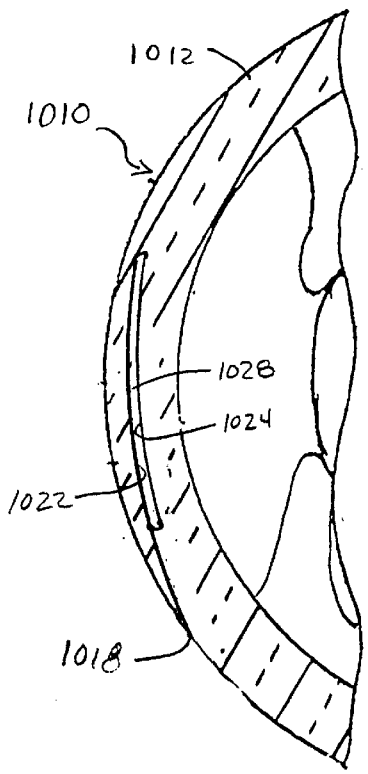
FIG. 65 is a side elevational view in longitudinal cross-section of the cornea shown in FIG. 64 illustrating the template positioned within the cornea.

As seen in FIG. 62, the first step of the procedure is to create an opening or incision 1018 into the epithelia of cornea 1012 as seen in FIGS. 62 and 63. Incision 1018 may be curved or straight and is preferably 2.0 mm to 4.0 mm long and about 3.0 mm to about 6.0 mm away from the center of cornea 1012. Of course, the size and location of incision 1018 depends upon the desired correction of cornea 1012. In other words, a plurality of incisions could be made if need or desired in accordance with the present invention. Incision 1018 or incisions can be made in cornea 1012 via a tool 1020, which can be any suitable instrument such as a fiber optic cable emitting in a laser beam, a scalpel, or a diamond tip micro drill.

Once incision 1018 is made, tool 1020 is inserted into the intrastromal area of cornea 1012 via incision 1018 to separate an internal area of live cornea 1012 into first and second opposed internal surfaces 1022 and 1024 to create an intrastromal or internal pocket 1026 as in the previous embodiments of FIGS. 19–27. Incision 1018 and pocket 1026 can be made in one single step by a laser or cutting mechanism, or in two steps as needed and or desired. First, internal surface 1022 faces in the posterior direction of eye 1010, while second internal surface 1024 faces in the anterior direction of eye 1010, and both of these surfaces extend radially relative to the center of cornea 1012.

Pocket 1026 can have its intrastromal tissue removed from either or both of internal surfaces 1022 and 1024. In other words, internal surfaces 1022 and 1024 of intrastromal pocket 1026 can be ablated or cut via tool 1020 to define a cavity. The ablating or removal of the internal surfaces 1022 and 1024 of the cornea is particularly desirable to remove opaque areas of cornea 1012. The removal of the intrastromal tissue from internal surfaces 1022 and 1024 can be accomplished by either a diamond tipped drill similar to FIG. 36 or via a laser beam-emitting cable such as a fiber optic cable similar to FIGS. 25–27.

Figure 66:
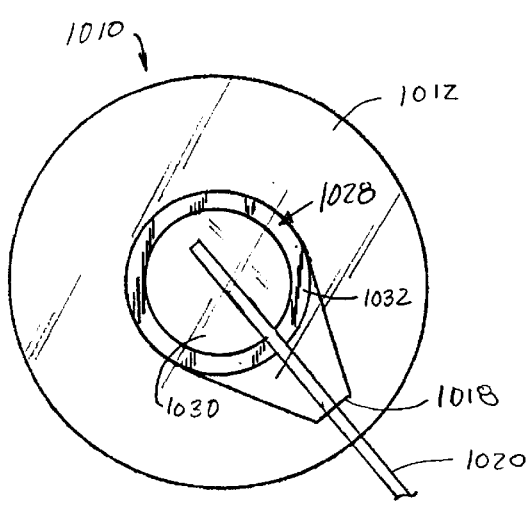
FIG. 66 is front elevation view of the live cornea illustrated in FIGS. 62–65, but with the template inserted within the cornea and a laser beam emitting cable or fiber optic cable inserted therein to ablate at least one of the first and second opposed internal surfaces of the live cornea.
Figure 68:
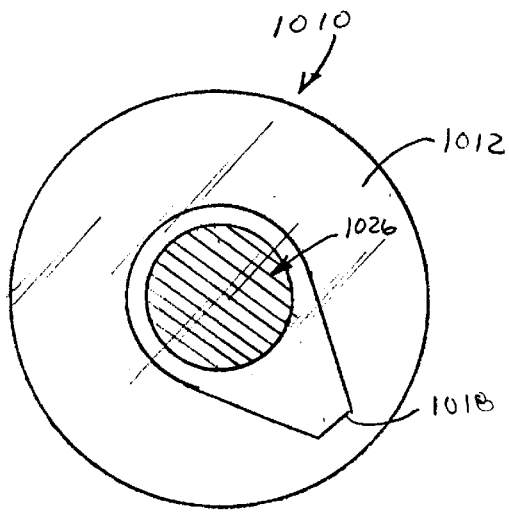
FIG. 68 is front elevational view of the live cornea illustrated in FIGS. 62–67 after one of the internal surfaces has been completely ablated to form a circular pocket.
Figure 67:
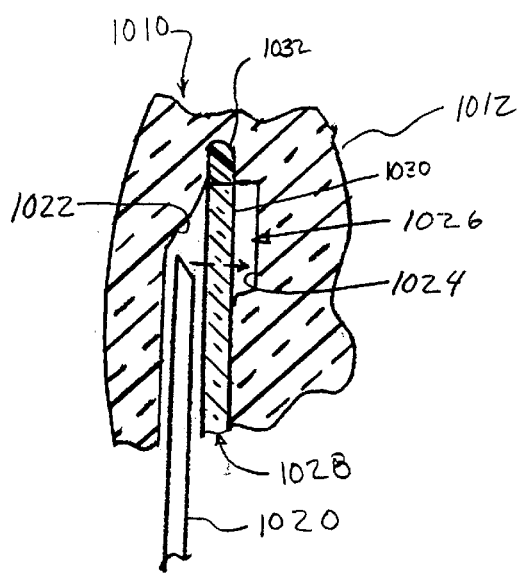
FIG. 67 is an enlarged, partial, side elevational view in section of the live cornea illustrated in FIG. 66 with the laser beam passing through a portion of the template to ablate one of the internal surfaces of the cornea.
Figure 69:
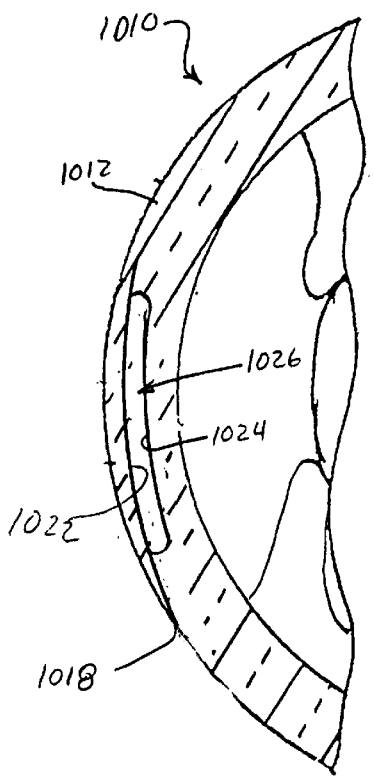
FIG. 69 is an enlarged side elevational view in cross section of the live cornea shown in FIG. 68 with a circular pocket formed therein and prior to collapsing thereof.
Figure 70:
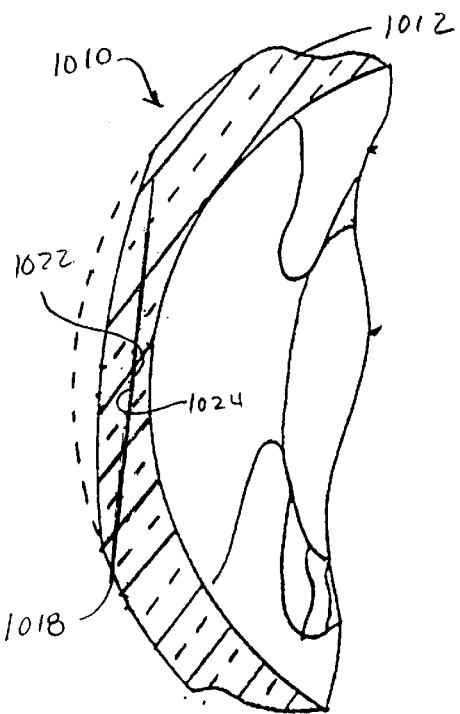
FIG. 70 is a side elevational view in cross section of the cornea shown in FIGS. 68 and 69, but after the ablated pocket has been collapsed to decrease the slope of the exterior surface of the cornea.

If tool 1020 is a fiber optic cable, then a template 1028 can be utilized to ablate internal surfaces 1022 and/or 1024 as seen in FIGS. 66 and 67. Template 1028 is preferably a flexible, resilient member including a laser beam transmitting portion 1030 and a laser beam blocking portion 1032 such that when the laser beam is directed onto the template, the laser beam passes through the laser beam transmitting portion 1030 but does not pass through the laser beam blocking portion 1032. In the example illustrated FIG. 64, template 1028 is circular with laser beam transmitting portion 1030 being substantially a disc-shaped member and laser beam blocking portion 1032 being ring-shaped and surrounding laser beam transmitting portion 1030. Accordingly, when the laser beam is directed onto template 1030, a disc-shaped portion is ablated from cornea 1012 as illustrated in FIGS. 67–69.

It will be apparent to those skilled in the art from this disclosure, that template 1028 can have a variety of shapes with laser beam transmitting portion 1030 and laser beam blocking portion 1032 being shaped to form any desired predetermined pattern for ablating the internal surfaces of 1022 and/or 1024 of cornea 1012. Moreover, laser beam transmitting portion 1030 can be merely a cutout in template 1028. Also, template 1028 can have slits to assist in the insertion of template 1028 into pocket 1026.

Figure 72:
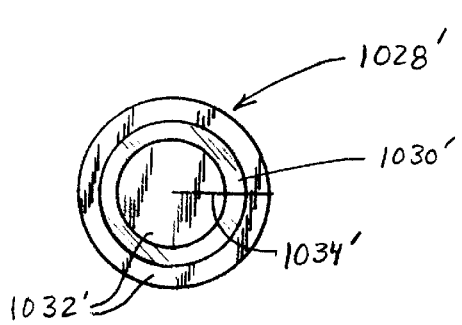
FIG. 72 is an alternative embodiment of a template for ablating at least one of the first and second opposed internal surfaces of the live cornea illustrated in FIGS. 62 and 63 so as to produce a ring-shaped ablation.
Figure 73:
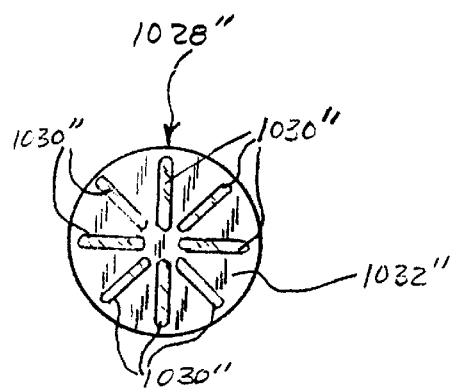
FIG. 73 is another alternative template for use in the live cornea illustrated in FIGS. 62 and 63 to ablate at least one of the first and second opposed internal surfaces in a plurality of radial lines.

Examples of other possible template configurations are shown in FIGS. 72 and 73 for controlling the ablation of cornea 1012. Template 1028' has a ring-shaped laser beam transmitting portion 1030' and a laser beam blocking portion 1032' surrounding portion 1030'. Template 1028' also has a slit 1034' for aiding in the insertion of template 1028' into cornea 1012. FIG. 73 illustrates a template 1028", which has a plurality of radially extending lines forming the laser beam transmitting portion 1030" and a laser beam blocking portion 1032" surrounding portion 1030".

It should also be apparent to those skilled in the art from this disclosure that the template to be used with the procedures of this invention may have a variety of shapes, including but not limited to partial disc shapes, partial ring shapes, irregular shapes, to obtain the desired ablation pattern.

Since template 1028 must be inserted through the relatively small opening or incision 1018, template 1028 must be able to be collapsed, e.g., folded or rolled, to fit through opening or incision 1018. Accordingly, template 1028 is created from a flexible resilient material, which can be collapsed for insertion into cornea 1012 via opening 1018 such that it can be easily restored to its original shape once in pocket 1026. Examples of various flexible materials include the same materials used for ocular implant 430, discussed above. By providing template 1028 with one or more slits, template 1028 can be easily collapsed for insertion into pocket 1026.

Once cornea 1012 has been ablated, cornea 1012 is left alone for a predetermined period of time such as twenty-four hours to about forty-eight hours to allow the cornea to obtain its new refractive powers. This predetermined period could be longer, e.g., up to one month or even slightly longer. Now the cornea 1012 is examined to determine how the cornea needs to be further modified to obtain the desired vision, if any further modification is needed. During this predetermined set time period, the pocket 1026 and the incision 1018 will not have time to completely heal such that the surgeon can further ablate the internal surfaces 1022 and/or 1024 of cornea 1012 and/or insert one of the previously ocular materials 428, 430, 528, 630 or 930, or any of the variations thereof as previously discussed above. In other words, the surgeon can further ablate cornea 1012 as necessary through small opening 1018 or insert the desired ocular material to create the desired further modification.

In the case of a solid ocular implant, the surgeon can insert one ocular implant and then examine the refractive power of cornea 1012 to determine if that is the correct ocular implant. If not, the surgeon can remove that ocular implant and insert another ocular implant. This procedure can be continued until the correct ocular implant is inserted into cornea 1012 via opening 1018. In other words, this procedure is somewhat similar to the eye examination procedure for receiving glasses or contact lenses, but wherein the surgeon is actually replacing lenses within a pocket or pockets of a cornea.

After the ablation, it is often desirable to irrigate pocket 1026 to remove any foreign matters and to clean pocket 1026. Such an irrigation step can be performed as many times as necessary in this procedure and at various times in the procedure as needed and/or desired.

Figure 71:
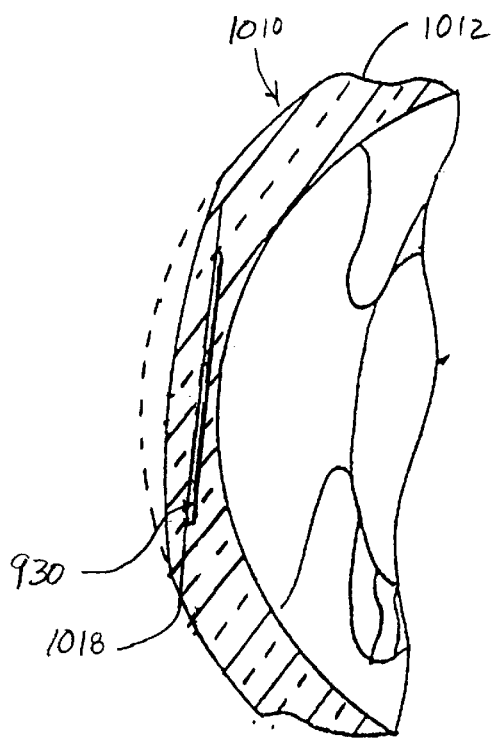
FIG. 71 is a side elevational view of the live cornea illustrated in FIG. 70, but with the ocular implant of FIGS. 60 and 61 inserted therein.

FIG. 71 illustrates cornea 1012 with ocular implant 930 inserted into pocket 1026. As mentioned above, ocular implant 930 is preferably a suitable transparent polymeric material utilizing diffractive technology, such as a Fresnel lens, which can be utilized to correct the focus of the light passing through the cornea by changing the refractive power of the cornea. The ocular implant 930 is particularly seen in FIGS. 60 and 61 and has a center opening 932 therein.

Of course, any one of the previously discussed ocular implants or materials can be utilized. In other words, the gel or fluid of the previous embodiments may be injected within the pocket 1026, and then the surgeon will examine the eye to determine the new refractive power of the cornea resulting from the insertion of the ocular material. Of course, the surgeon can adjust the ocular material by adding or subtracting predetermined amounts of the ocular material, and then reexamining the patient's eye until the desired refractive power of the cornea is obtained.

Of course, the curvature of the cornea can be modified as needed by the insertion of the ocular material in the same manner as mentioned previously herein and as illustrated in the previously discussed figures. In particular, as seen in the previous examples of FIGS. 38–40 utilizing ocular material 428, pocket 1026 can be overfilled, partially filled, or completely filled to modify cornea 1012 as needed. The cavity or pocket 1026 can be completely filled with the ocular material to restore the normal curvature of the cornea 1026 to result in a cornea with a curvature similar to cornea 428 as seen in FIG. 40. The amount of ocular material introduced to pocket 1026 can be increased to increase the curvature of cornea 1012 from its original curvature to treat hypermyopia so as to result in a cornea with a curvature as seen in FIG. 38. Alternatively, the amount of ocular material introduced into pocket 1026 can be reduced to decrease the curvature or flatten cornea 1012 from its original curvature to treat myopia so as to result in a cornea with a curvature as seen in FIG. 39.

In the case of a solid resilient ocular implant, cornea 1012 can result in various curvature modifications similar to those seen in FIGS. 43–45. In the case of utilizing an ocular implant such as the ring-shaped ocular implant of FIGS. 41 and 42 or a partial ring-shaped ocular implant as previously mentioned, the template of FIG. 72 may be useful.

After the pocket 1026 has the proper ocular material inserted or injected therein, the internal surfaces 1022 and 1024 of pocket 1026 come together to encapsulate ocular material within cornea 1012. In other words, the surfaces heal and grow back together, resulting in permanent curvature modification of the cornea.

While various advantageous embodiments have been chosen to illustrate the invention, it will be understood by those skilled in the art that various changes and modifications can be made therein without departing from the scope of the invention as defined in the appended claims.

What is claimed is:

1. A method of modifying the curvature of a patient's live cornea having an exterior surface, comprising the steps of forming a relatively small opening in the exterior surface of the live cornea, separating an internal area of the live cornea into first and second opposed internal surfaces via the opening to form a pocket, the first internal surface facing in a posterior direction of the live cornea and the second internal surface facing in an anterior direction of the live cornea, inserting a template through the opening in the exterior surface of the live cornea, the template having a laser beam transmitting portion and a laser beam blocking portion for forming a predetermined template pattern, inserting a portion of a laser beam-emitting cable through the opening between the first and second internal surfaces, directing a laser beam from the laser beam-emitting cable onto the template so that the laser beam passes through the laser beam transmitting portion of the template and onto at least one of the first and second internal surfaces in a predetermined pattern to incrementally ablate and completely remove three-dimensional portions sequentially thereof, and permitting the pocket, after ablation, to collapse and the live cornea to heal.

2. A method according to claim 1 wherein the opening formed in the exterior surface of the cornea is about 3 mm to about 4 mm.

3. A method according to claim 2, further comprising the steps of collapsing the template prior to inserting the template through the opening and into the pocket, and then restoring the template to its original shape within the pocket.

4. A method according to claim 1, further comprising the step of inserting ocular material into the pocket after the step of directing a laser beam onto the template.

5. A method according to claim 4, wherein the ocular material is a fluid.

6. A method according to claim 4, wherein the ocular material is a resilient ocular implant.

7. A method according to claim 4, wherein the ocular material is sized and positioned between the first and second internal surfaces to reduce the curvature of the cornea.

8. A method according to claim 4, wherein the ocular material is sized and positioned between the first and second surfaces to increase the curvature of the cornea.

9. A method according to claim 4, wherein the ocular material is sized and positioned between the first and second surfaces to substantially maintain the cornea's original curvature.

10. A method according to claim 4, wherein the ocular material is a corrective lens with at least a portion of the ocular implant having a refractive index different from that of the cornea.

11. A method according to claim 4, further comprising the steps of waiting a period of time to allow the cornea to collapse to its new refractive power prior to inserting the ocular material, and examining the live cornea prior to inserting the ocular material to determine the new refractive power of the live cornea resulting from removal of internal portions of the live cornea.

* * * * *

UNITED STATES PATENT AND TRADEMARK OFFICE
CERTIFICATE OF CORRECTION

PATENT NO. : 6,203,538 B1
DATED : March 20, 2001
INVENTOR(S) : Gholam A. Peyman

It is certified that error appears in the above-identified patent and that said Letters Patent is hereby corrected as shown below:

<u>Title page,</u>
Please change the Related U.S. Application Data, Item [62] to read -- Division of Application No. 08/552,624, filed November 3, 1995 now Patent No. 5,722,971. --

Signed and Sealed this

Sixteenth Day of October, 2001

Attest:

NICHOLAS P. GODICI
Attesting Officer
*Acting Director of the United States Patent and Trademark Office*